(12) United States Patent
Nakashima et al.

(10) Patent No.: US 7,666,524 B2
(45) Date of Patent: Feb. 23, 2010

(54) OLIGONAPHTHALENE DERIVATIVES, AND LIGHT-EMITTING ELEMENT AND LIGHT-EMITTING DEVICE USING OLIGONAPHTHALENE DERIVATIVES

(75) Inventors: Harue Nakashima, Atsugi (JP); Sachiko Kawakami, Atsugi (JP); Ryoji Nomura, Yamato (JP)

(73) Assignee: Semiconductor Energy Laboratory Co., Ltd., Atsugi-shi, Kanagawa-ken (JP)

( * ) Notice: Subject to any disclaimer, the term of this patent is extended or adjusted under 35 U.S.C. 154(b) by 441 days.

(21) Appl. No.: 11/249,362

(22) Filed: Oct. 14, 2005

(65) Prior Publication Data
US 2006/0093857 A1    May 4, 2006

(30) Foreign Application Priority Data
Oct. 29, 2004    (JP)    .............................. 2004-315669

(51) Int. Cl.
  *H01L 51/54*    (2006.01)
  *C09K 11/06*    (2006.01)
(52) U.S. Cl. ........................ 428/690; 428/917; 313/504; 313/506; 252/301.16; 257/40; 257/E51.027; 560/100; 568/328
(58) Field of Classification Search .................... 585/4, 585/5, 6, 24, 25, 26; 428/690, 917; 313/504, 313/506; 257/40, E51.044, E51.049; 564/429; 556/431, 432, 465
See application file for complete search history.

(56) References Cited

U.S. PATENT DOCUMENTS

| | | | |
|---|---|---|---|
| 5,935,721 A | 8/1999 | Shi et al. | |
| 6,203,933 B1 * | 3/2001 | Nakaya et al. | .............. 428/690 |
| 6,225,467 B1 * | 5/2001 | Esteghamatian et al. | .... 544/180 |
| 6,534,199 B1 | 3/2003 | Hosokawa et al. | |
| 6,660,408 B1 * | 12/2003 | Toguchi et al. | .............. 428/690 |
| 2001/0021478 A1 * | 9/2001 | Shi et al. | ................... 430/57.1 |
| 2002/0045061 A1 * | 4/2002 | Hosokawa | ................. 428/690 |
| 2004/0142206 A1 | 7/2004 | Bazan et al. | |
| 2004/0151945 A1 | 8/2004 | Bazan et al. | |
| 2005/0175857 A1 * | 8/2005 | Coggan et al. | .............. 428/690 |

FOREIGN PATENT DOCUMENTS

| | | |
|---|---|---|
| EP | 1 167 488 | 1/2002 |
| EP | 1 580 250 | 9/2005 |
| JP | 2005-019219 | 1/2005 |
| WO | WO 2004/067675 | 8/2004 |

OTHER PUBLICATIONS

T. Hayashi et al., *Asymmetric Synthesis of Axially Chiral 1,1′:5′,1″—and 1,1′:4′,1″—Temaphthalenes by Asymmetric Cross-Coupling with a Chiral Ferrocenylphosphine-Nickel Catalyst*, Tetrahedron Letters, vol. 30, No. 2, pp. 215-218, 1989.
European Search Report dated Feb. 14, 2006 for Application No. 05023304.8.

* cited by examiner

*Primary Examiner*—D. Lawrence Tarazano
*Assistant Examiner*—Michael Wilson
(74) *Attorney, Agent, or Firm*—Eric J. Robinson; Robinson Intellectual Property Law Office, P.C.

(57) ABSTRACT

The present invention provides a novel material capable of realizing excellent color purity of blue, a light-emitting element and a light-emitting device using the novel material. The present invention provides an oligonaphthalene derivative represented by the formula (1). The oligonaphthalene derivatives of the present invention have an extremely large band gap, can emit light with extremely short wavelength, and can emit blue light with favorable color purity. In addition, a light-emitting element that can exhibit excellent color purity of blue can be obtained by applying this material to the light-emitting element or a light-emitting device; therefore the light-emitting element having superior color reproducibility can be provided.

3 Claims, 10 Drawing Sheets

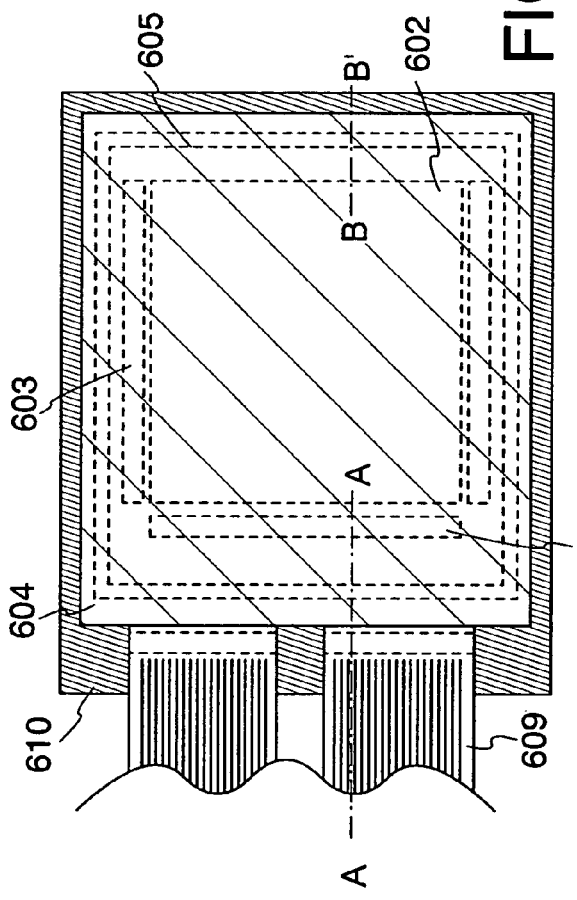
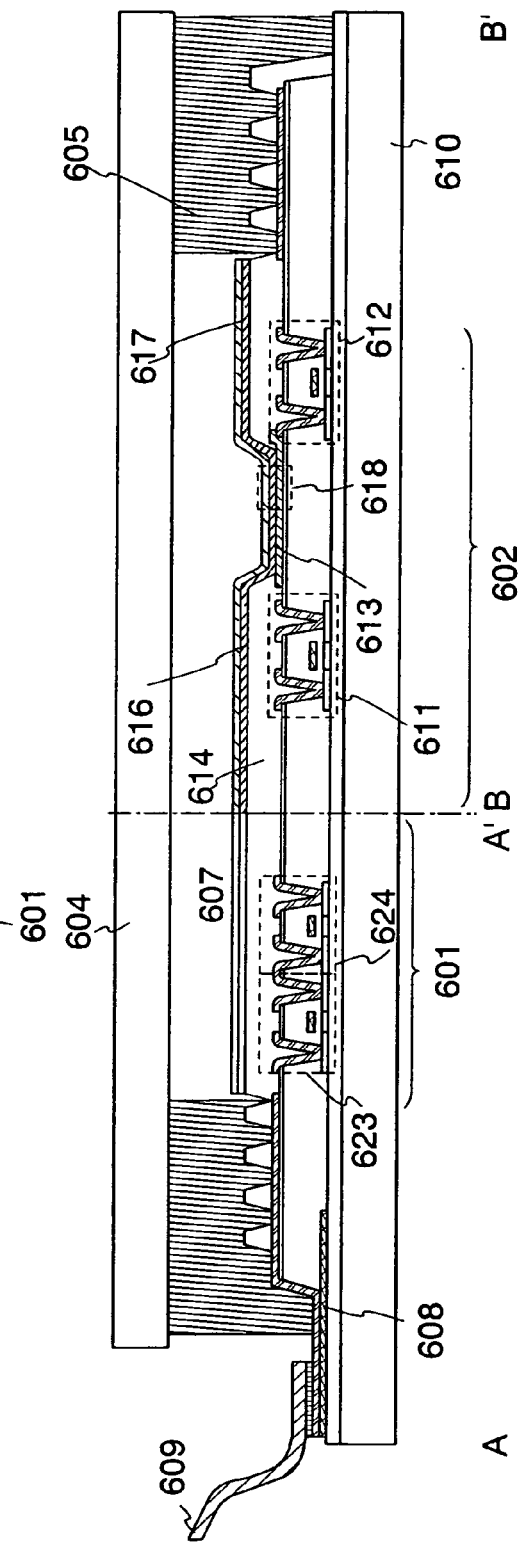
FIG. 11A
FIG. 11B

OLIGONAPHTHALENE DERIVATIVES, AND LIGHT-EMITTING ELEMENT AND LIGHT-EMITTING DEVICE USING OLIGONAPHTHALENE DERIVATIVES

BACKGROUND OF THE INVENTION

1. Field of the Invention

The present invention relates to a luminescent material. Further, the present invention relates to a light-emitting element having a pair of electrodes, a layer including a luminescent material that can emit light by being applied with electric field. Moreover, the present invention relates to a light-emitting device having such a light-emitting element.

2. Description of the Related Art

A light-emitting element using a luminescent material has advantages of thinness, lightness in weight, fast response, direct-current low-voltage driving, and so on, and is expected to be applied to a next-generation flat panel display. Further, a light-emitting device having light-emitting elements arranged in matrix is superior to a conventional liquid crystal display device in a wide viewing angle and high visibility.

A light-emitting element has the following light-emission mechanism; voltage is applied to a light-emitting layer sandwiched between a pair of electrodes, electrons injected from a cathode and holes injected from an anode are recombined in a light-emission center of the light-emitting layer to form molecular excitons, and then light is emitted by releasing energy when the molecular exciton returns to the ground state. As the excited state, a singlet-excited state and a triplet-excited state are known, and the light emission is possible by either of the excited states.

Emission wavelength of a light-emitting element is determined by energy difference between a ground state and an excited state, i.e., a band gap, of a light-emitting molecule included in the light-emitting element. Therefore, various emission colors can be obtained by devising structures of the light-emitting molecules. By forming a light-emitting device using light-emitting elements capable of emitting red light, blue light and green light, which are light's three primary colors, a full-color light-emitting device can be manufactured.

However, there is a problem of such a full-color light-emitting device. The problem is that formation of a light-emitting element having excellent color purity is not easy. This is because it is difficult to realize a light-emitting element with high reliability and excellent color purity, although light-emitting elements for red, blue and green with excellent color purity are needed so as to manufacture a light-emitting device having superior color reproducibility. As a result of recent development of materials, light-emitting elements for red and green have achieved high reliability and excellent color purity. However, in particular, a light-emitting element for blue cannot be realized high reliability and excellent color purity.

SUMMARY OF THE INVENTION

The present invention has been made in view of the above described problem. It is an object of the present invention to provide a novel material capable of realizing excellent color purity of blue, and a light-emitting element and a light-emitting device using the novel material.

The present inventors have found that an oligonaphthalene derivative represented by the following formula (1) can exhibit light-emission with excellent color purity of blue.

Therefore, the present invention provides the oligonaphthalene derivative represented by the following formula (1):

(1)

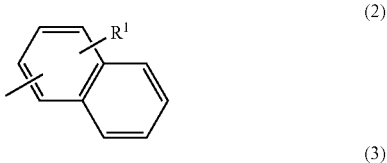
(2)

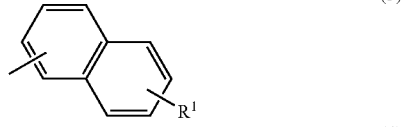
(3)

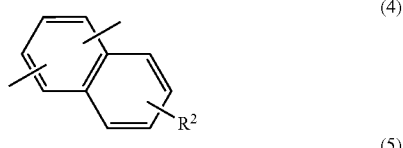
(4)

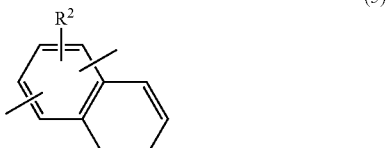
(5)

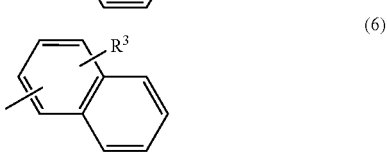
(6)

(7)

wherein, n is 1 or 2, $Ar^1$ is a substituent represented by a formula (2) or (3), $Ar^2$ is a substituent represented by a formula (4) or (5), $Ar^3$ is a substituent represented by a formula (6) or (7), and $R^1$ to $R^3$ are independently hydrogen, a linear or branched alkyl group having 6 or fewer carbon atoms, an alicyclic alkyl group, a substituted or unsubstituted aromatic ring, a substituted or unsubstituted hetero aromatic ring, an alkoxy group, an amino group, a cyano group, a silyl group, an ester group, a carbonyl group or halogen.

The present invention provides an oligonaphthalene derivative shown by a formula (8):

(8)

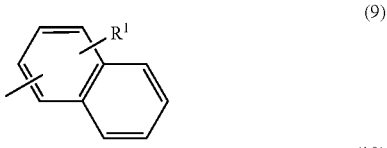
(9)

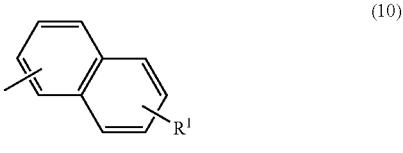
(10)

-continued

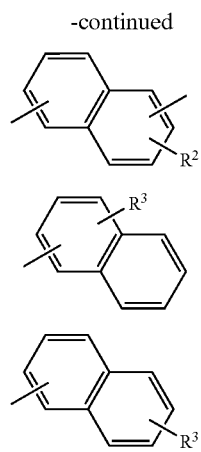

(11)

(12)

(13)

wherein n is 1 or 2, Ar¹ is a substituent represented by a formula (9) or (10), Ar² is a substituent represented by a formula (11), Ar³ is a substituent represented by a formula (12) or (13), and R¹ to R³ are independently hydrogen, a linear or branched alkyl group having 6 or fewer carbon atoms, an alicyclic alkyl group, a substituted or unsubstituted aromatic ring, a substituted or unsubstituted hetero aromatic ring, an alkoxy group, an amino group, a cyano group, a silyl group, an ester group, a carbonyl group, or halogen.

The oligonaphthalene derivative shown by formula (14) is preferable:

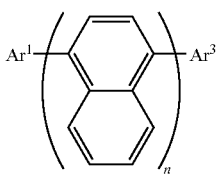

(14)

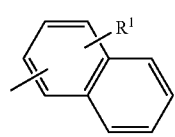

(15)

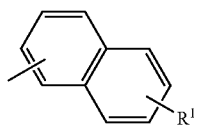

(16)

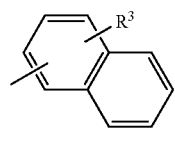

(17)

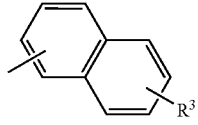

(18)

wherein n is 1 or 2, Ar¹ is a substituent represented by a formula (15) or (16), Ar³ is a substituent represented by a formula (17) or (18), and R¹ and R³ are independently hydrogen, a linear or branched alkyl group having 6 or fewer carbon atoms, an alicyclic alkyl group, a substituted or unsubstituted aromatic ring, a substituted or unsubstituted hetero aromatic ring, an alkoxy group, an amino group, a cyano group, a silyl group, an ester group, a carbonyl group, or halogen.

Further, the oligonaphthalene derivative represented by a formula (19) is preferable:

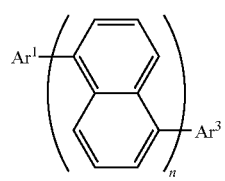

(19)

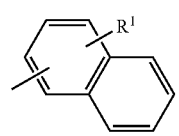

(20)

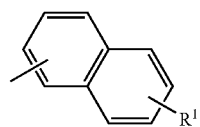

(21)

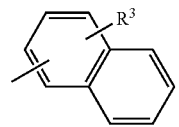

(22)

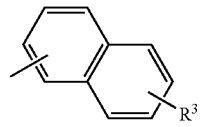

(23)

wherein n is 1 or 2, Ar¹ is a substituent represented by a formula (20) or (21), Ar³ is a substituent represented by a formula (22) or (23), and R¹ and R³ are independently hydrogen, a linear or branched alkyl group having 6 or fewer carbon atoms, an alicyclic alkyl group, a substituted or unsubstituted aromatic ring, a substituted or unsubstituted hetero aromatic ring, an alkoxy group, an amino group, a cyano group, a silyl group, an ester group, a carbonyl group, or halogen.

In particular, the oligonaphthalene derivative shown by a formula (24) is preferable:

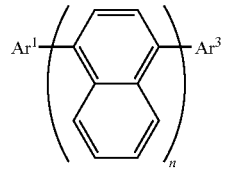

(24)

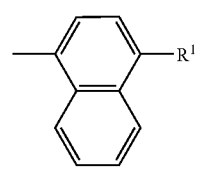

(25)

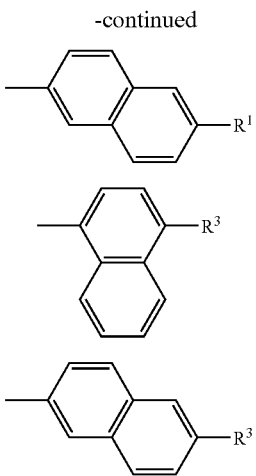

(26)
(27)
(28)

wherein n is 1 or 2, Ar¹ is a substituent represented by a formula (25) or (26), Ar³ is a substituent represented by a formula (27) or (28), and $R^1$ and $R^3$ are independently hydrogen, a linear or branched alkyl group having 6 or fewer carbon atoms, an alicyclic alkyl group, a substituted or unsubstituted aromatic ring, a substituted or unsubstituted hetero aromatic ring, an alkoxy group, an amino group, a cyano group, a silyl group, an ester group, a carbonyl group, or halogen.

Also, the oligonaphthalene derivatives shown by a formula (29) is preferable.

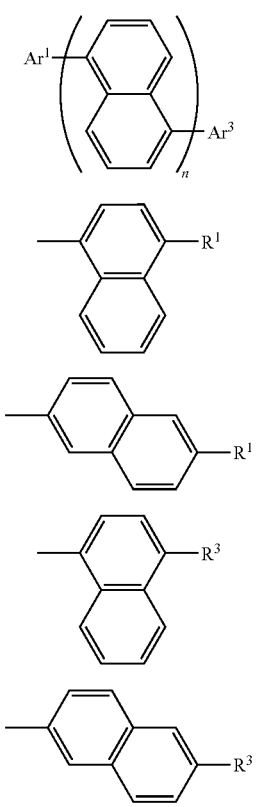

(29)
(30)
(31)
(32)
(33)

wherein n is 1 or 2, Ar¹ is a substituent represented by a formula (30) or (31), Ar³ is a substituent represented by a formula (32) or (33), and $R^1$ and $R^3$ are independently hydrogen, a linear or branched alkyl group having 6 or fewer carbon atoms, an alicyclic alkyl group, a substituted or unsubstituted aromatic ring, a substituted or unsubstituted hetero aromatic ring, an alkoxy group, an amino group, a cyano group, a silyl group, an ester group, a carbonyl group, or halogen.

One feature of an oligonaphthalene derivative of the present invention is that the oligonaphthalene derivative has the maximum emission peak of 350 to 450 nm.

In addition, a light-emitting element of the present invention includes a layer having a luminescent material between a pair of electrodes, and the layer including a luminescent material includes the oligonaphthalene derivatives.

The present invention includes a light-emitting device having such a light-emitting element described above in the category.

The oligonaphthalene derivatives according to the present invention have an extremely large band gap, can emit light with extremely short wavelength, and can emit blue light with favorable color purity.

By using oligonaphthalene derivatives of the present invention as a luminescent material of a light-emitting element, a light-emitting element that can provide excellent color purity of blue can be obtained.

A luminescent material (hereinafter, dopant) having a band gap smaller than the oligonaphthalene derivatives of the present invention may be added into a layer including the oligonaphthalene derivatives of the present invention to obtain luminescence from the dopant. At this time, since the oligonaphthalene derivative of the present invention has an extremely large band gap, even if a dopant emitting light of a relatively short wavelength is used, luminescence from the dopant can be obtained efficiently instead of luminescence from the oligonaphthalene derivative of the present invention. Specifically, a luminescent material having a maximum emission wavelength around 450 nm provides excellent color purity of blue, and such a material can be used as a dopant.

In addition, since a luminescent material using a material of the present invention has excellent color purity of blue, a light-emitting device using a light-emitting element of the present invention has superior color reproducibility.

BRIEF DESCRIPTION OF THE DRAWINGS

FIGS. 11A and 11B each show a light-emitting device according to one aspect of the present invention.

DETAILED DESCRIPTION OF THE INVENTION

Figure 1:
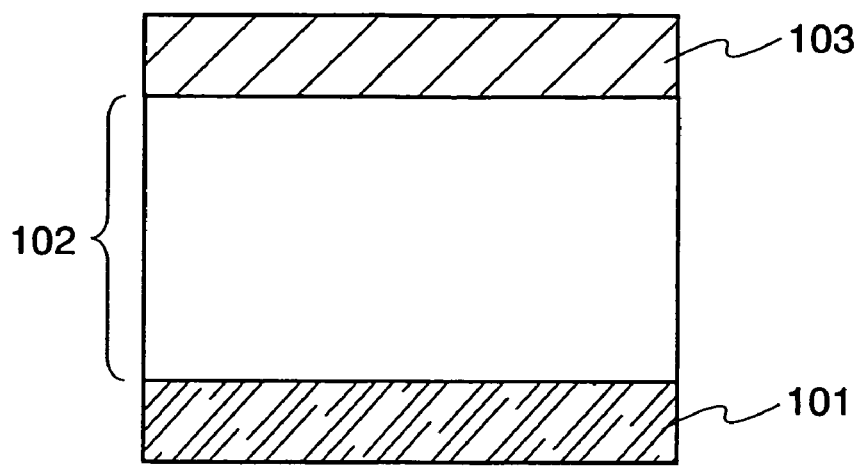
FIG. 1 is a diagram of a light-emitting element according to one aspect of the present invention.

Embodiments according to the present invention will hereinafter be described with reference to the accompanying drawings. The present invention is not limited to the following description. The present invention can be carried out in many different modes, and it is easily understood by those skilled in the art that modes and details herein disclosed can be modified in various ways without departing from the spirit and the scope of the present invention. It should be noted that the present invention should not be interpreted as being limited to the description of the embodiments to be given below.

EMBODIMENT 1

Materials of the present invention are described in Embodiment 1.

An oligonaphthalene derivative of the present invention has a structure represented by the formula (1).

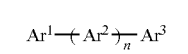  (1)

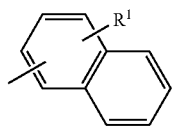  (2)

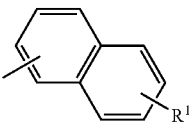  (3)

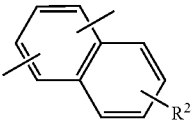  (4)

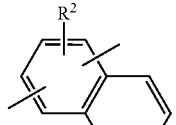  (5)

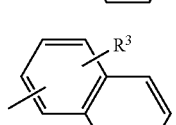  (6)

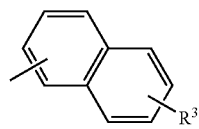  (7)

wherein n is 1 or 2, $Ar^1$ is a substituent represented by the formula (2) or (3), $Ar^2$ is a substituent represented by the formula (4) or (5), $Ar^3$ is a substituent represented by the formula (6) or (7), and $R^1$ to $R^3$ are independently hydrogen, a linear or branched alkyl group having 6 or fewer carbon atoms, an alicyclic alkyl group, a substituted or unsubstituted aromatic ring, a substituted or unsubstituted hetero aromatic ring, an alkoxy group, an amino group, a cyano group, a silyl group, an ester group, a carbonyl group, or halogen.

An oligonaphthalene derivative of the present invention has a structure represented by the formula (8).

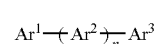  (8)

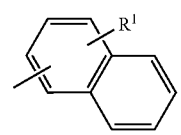  (9)

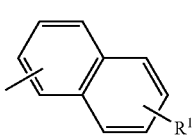  (10)

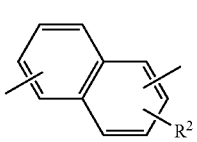  (11)

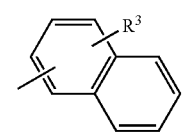  (12)

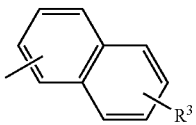  (13)

wherein n is 1 or 2, $Ar^1$ is a substituent represented by the formula (9) or (10), $Ar^2$ is a substituent represented by the formula (11), $Ar^3$ is a substituent represented by the formula (12) or (13), and $R^1$ to $R^3$ are independently hydrogen, a linear or branched alkyl group having 6 or fewer carbon atoms, an alicyclic alkyl group, a substituted or unsubstituted aromatic ring, a substituted or unsubstituted hetero aromatic ring, an alkoxy group, an amino group, a cyano group, a silyl group, an ester group, a carbonyl group, or halogen.

Specifically, an oligonaphthalene derivative of the present invention has a structure represented by the formula (14).

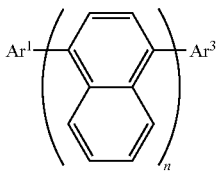
(14)

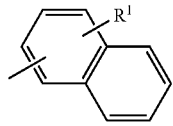
(15)

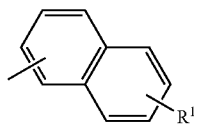
(16)

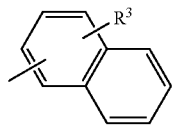
(17)

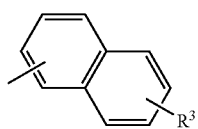
(18)

wherein n is 1 or 2, $Ar^1$ is a substituent represented by the formula (15) or (16), $Ar^3$ is a substituent represented by the formula (17) or (18), and $R^1$ and $R^3$ are independently hydrogen, a linear or branched alkyl group having 6 or fewer carbon atoms, an alicyclic alkyl group, a substituted or unsubstituted aromatic ring, a substituted or unsubstituted hetero aromatic ring, an alkoxy group, an amino group, a cyano group, a silyl group, an ester group, a carbonyl group, or halogen.

In addition, an oligonaphthalene derivative of the present invention has a structure represented by the formula (19).

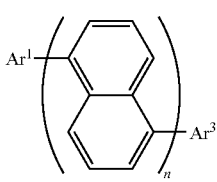
(19)

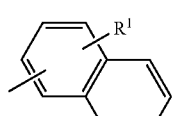
(20)

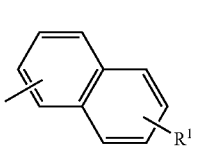
(21)

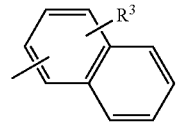
(22)

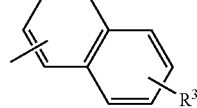
(23)

wherein n is 1 or 2, $Ar^1$ is a substituent represented by the formula (20) or (21), $Ar^3$ is a substituent represented by the formula (22) or (23), and $R^1$ and $R^3$ are independently hydrogen, a linear or branched alkyl group having 6 or fewer carbon atoms, an alicyclic alkyl group, a substituted or unsubstituted aromatic ring, a substituted or unsubstituted hetero aromatic ring, an alkoxy group, an amino group, a cyano group, a silyl group, an ester group, a carbonyl group, or halogen.

Specifically, an oligonaphthalene derivative of the present invention has a structure represented by the formula (24).

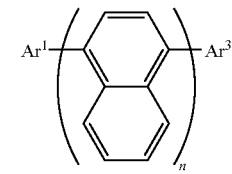
(24)

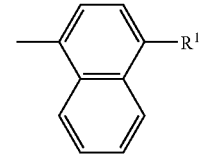
(25)

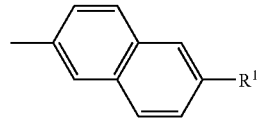
(26)

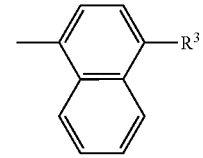
(27)

(28)

wherein n is 1 or 2, $Ar^1$ is a substituent represented by the formula (25) or (26), $Ar^3$ is a substituent represented by the formula (27) or (28), and $R^1$ and $R^3$ are independently hydrogen, a linear or branched alkyl group having 6 or fewer carbon atoms, an alicyclic alkyl group, a substituted or unsubstituted aromatic ring, a substituted or unsubstituted hetero aromatic ring, an alkoxy group, an amino group, a cyano group, a silyl group, an ester group, a carbonyl group, or halogen.

Moreover, an oligonaphthalene derivative of the present invention preferably has a structure represented by the formula (29).

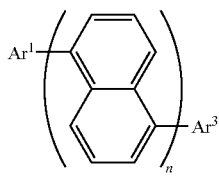
(29)

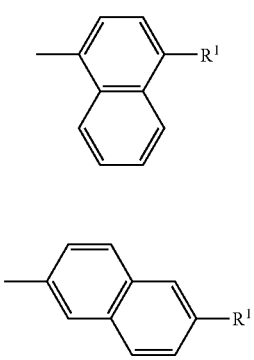
(30)

(31)

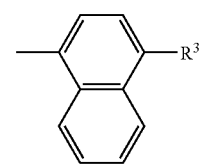
(32)

(33)

wherein n is 1 or 2, $Ar^1$ is a substituent represented by the formula (30) or (31), $Ar^3$ is a substituent represented by the formula (32) or (33), and $R^1$ and $R^3$ are independently hydrogen, a linear or branched alkyl group having 6 or fewer carbon atoms, an alicyclic alkyl group, a substituted or unsubstituted aromatic ring, a substituted or unsubstituted hetero aromatic ring, an alkoxy group, an amino group, a cyano group, a silyl group, an ester group, a carbonyl group, or halogen.

Specific examples of the alkyl group having 6 or fewer carbon atoms are a methyl group, an ethyl group, an n-propyl group, an i-propyl group, an n-butyl group, an i-butyl group, a sec-butyl group, a t-butyl group, an n-pentyl group, an i-pentyl group, an n-hexyl group, and the like.

Specific examples of the alicyclic alkyl group are a cyclopropyl group, an cyclobutyl group, a cyclopentyl group, a cyclohexyl group and the like.

Specific examples of the substituted or unsubstituted aromatic ring are a phenyl group, a naphthyl group, an anthranyl group, a pyrenyl group, a spirofluorenyl group and the like.

Specific groups of the substituted or unsubstituted hetero aromatic ring are a pyridyl group, an indolyl group, a carbazolyl group, a thienyl group, a furyl group and the like.

The oligonaphthalene derivatives represented by the following structural formulas (34) to (144) are given as specific examples of the oligonaphthalene derivative represented by the formula (1). However, the present invention is not limited to the examples.

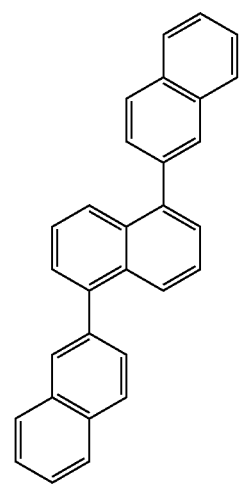
(34)

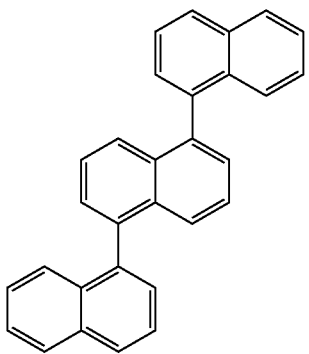
(35)

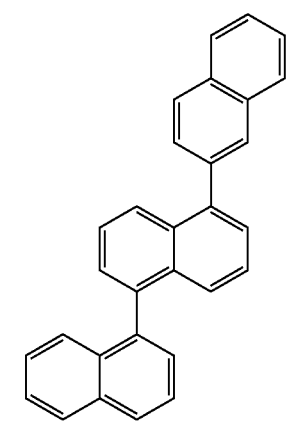
(36)

-continued
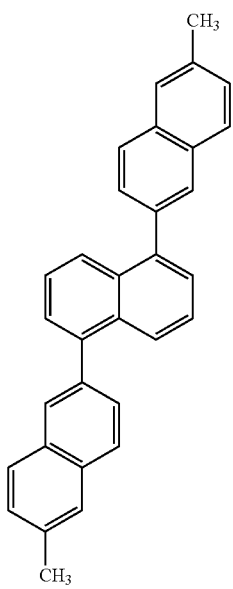
(37)
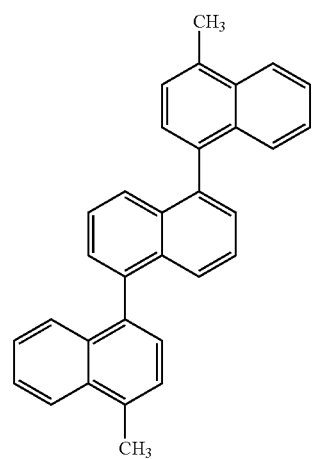
(38)
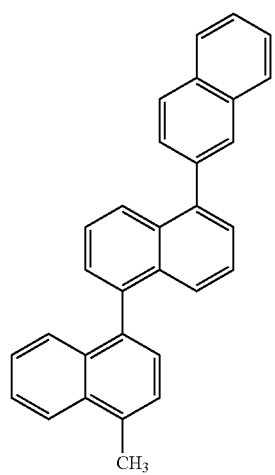
(39)
-continued
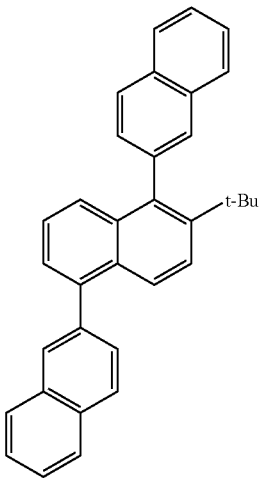
(40)
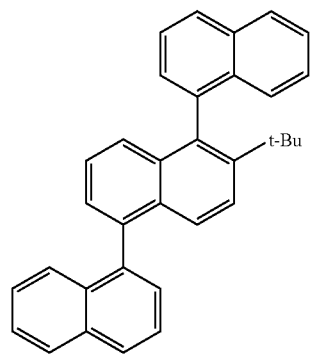
(41)
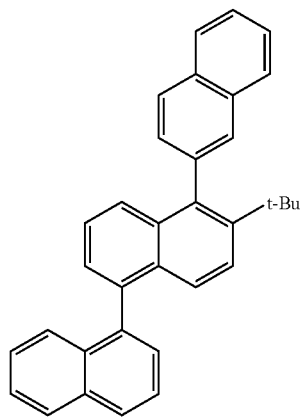
(42)

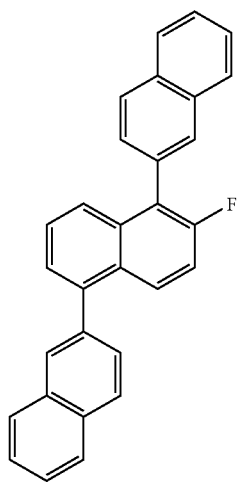
(43)
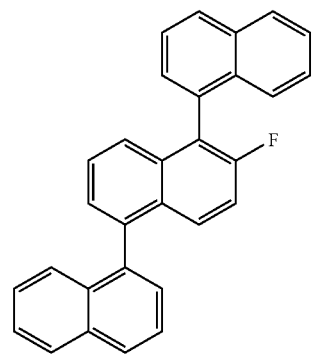
(44)
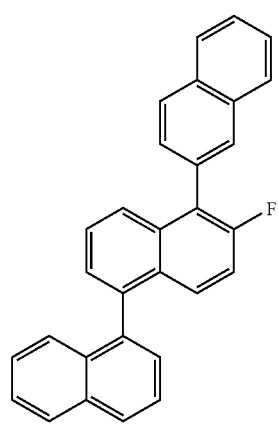
(45)
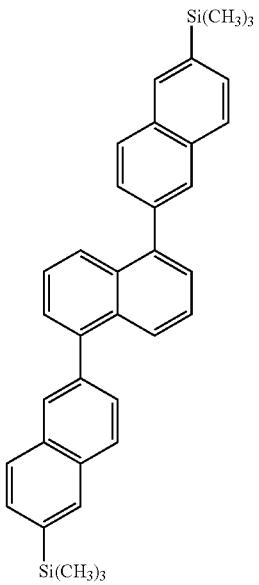
(46)
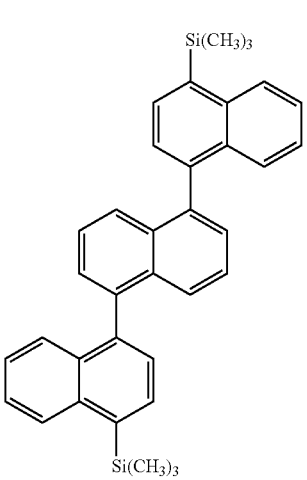
(47)
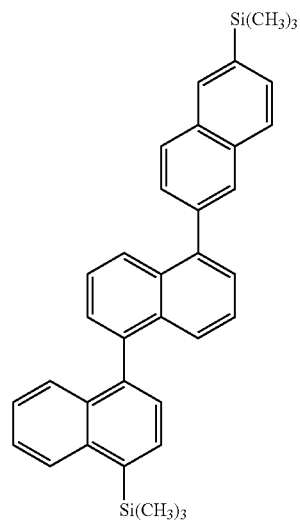
(48)

-continued
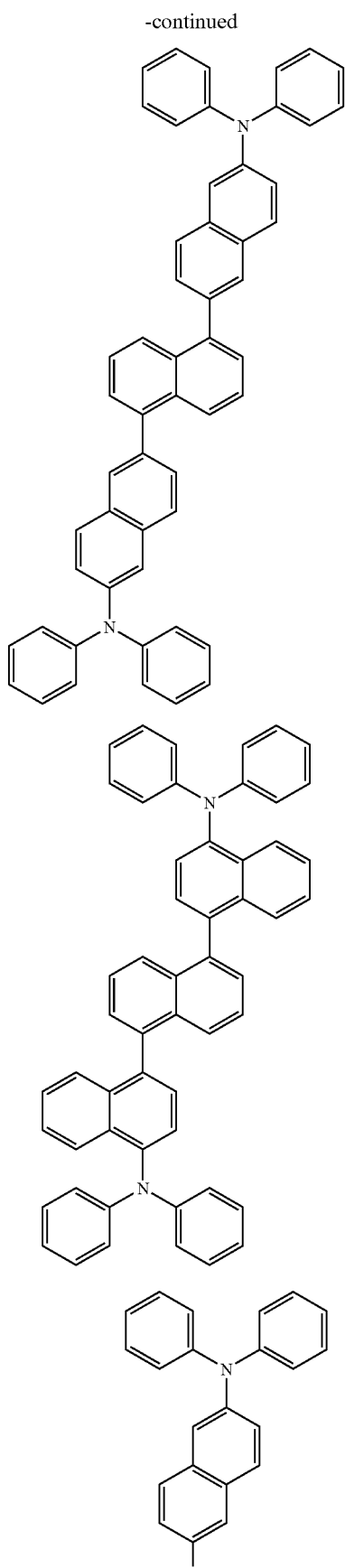
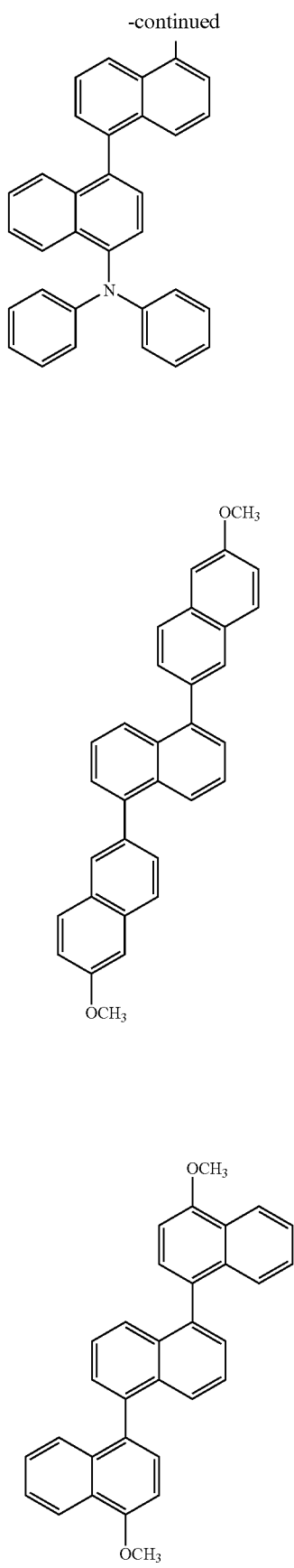

-continued
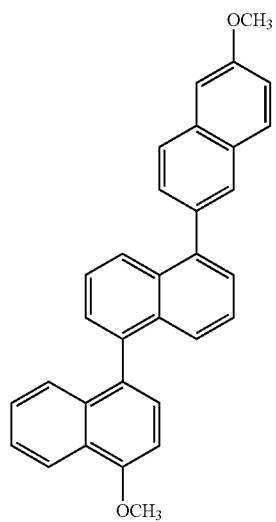
(54)
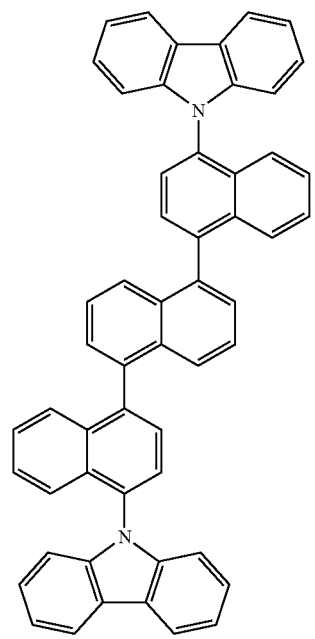
(56)
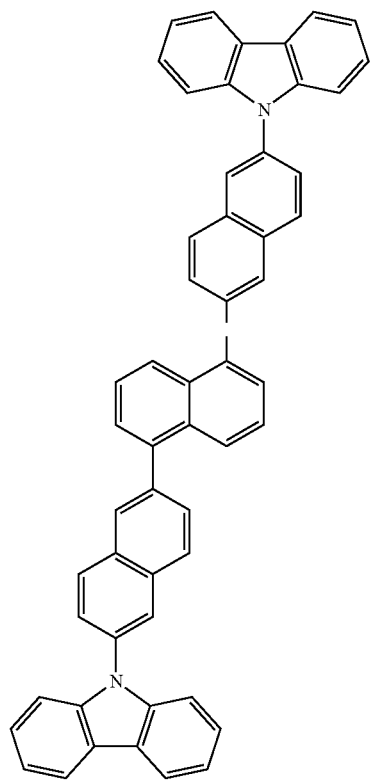
(55)
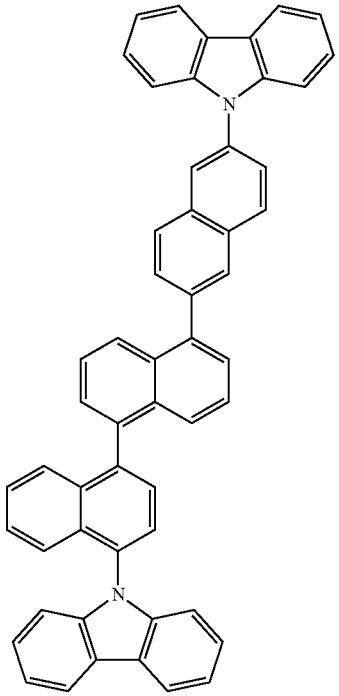
(57)

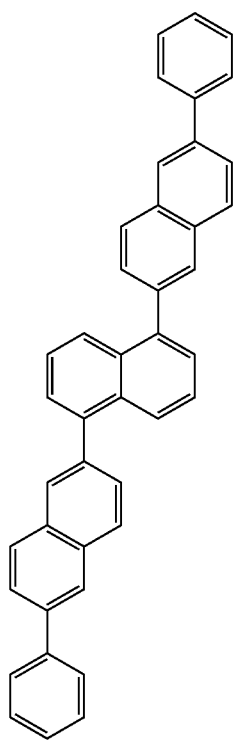
(58)
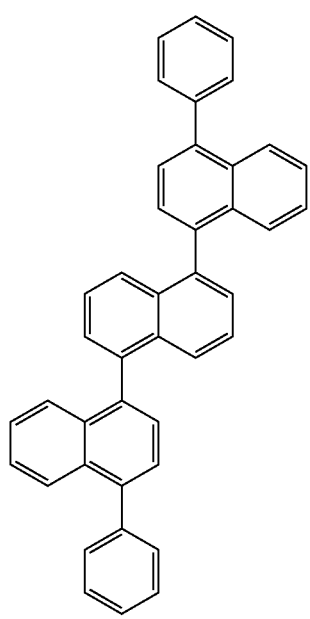
(59)
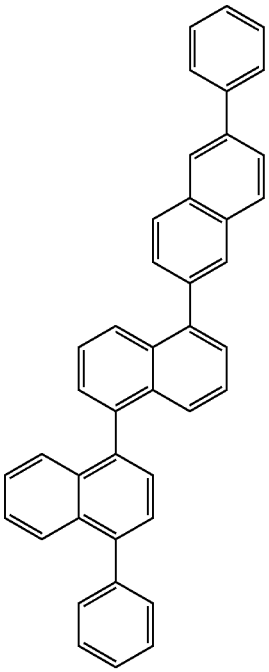
(60)
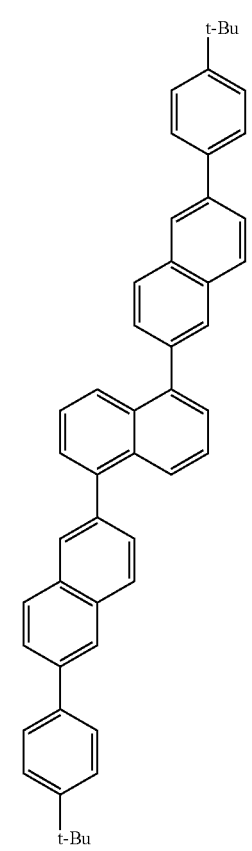
(61)

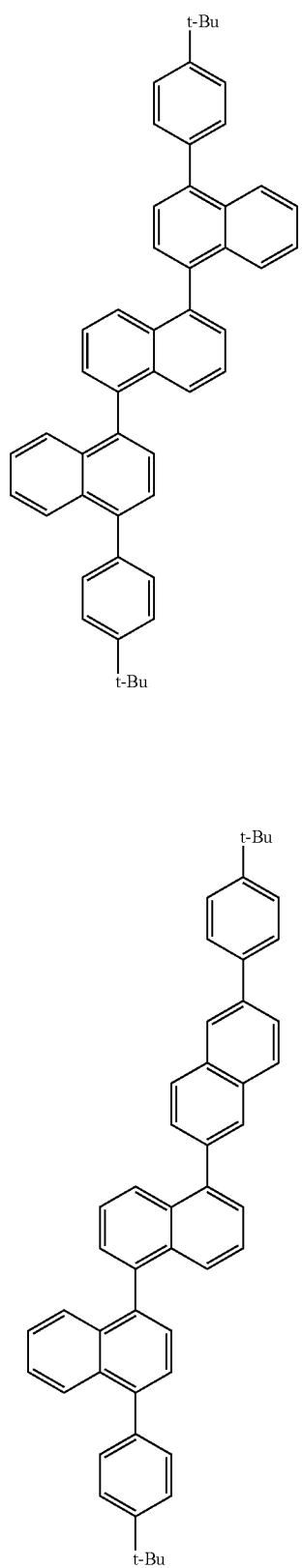 (62)
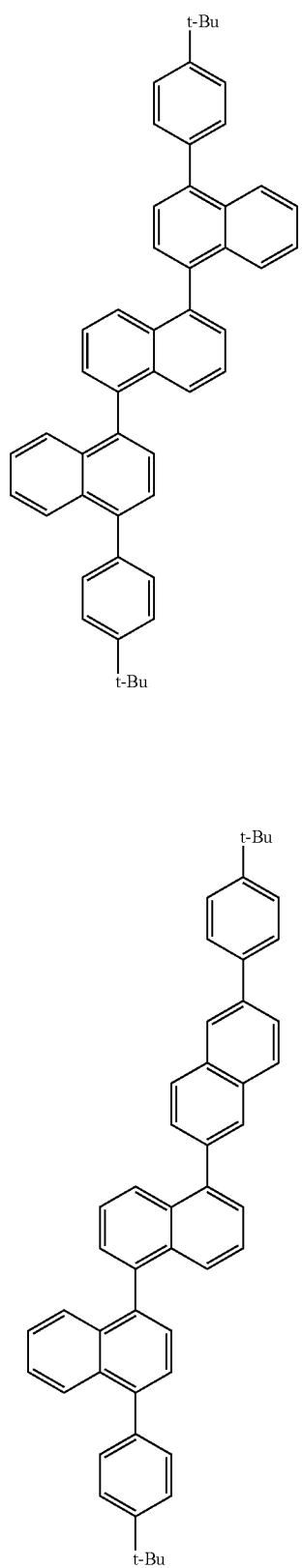 (63)
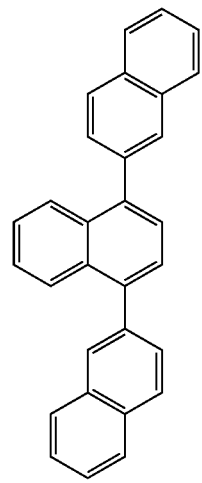 (64)
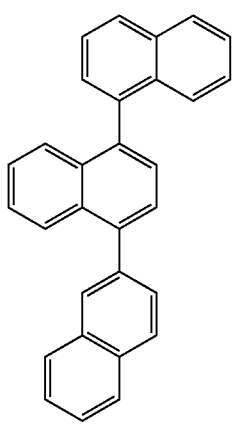 (65)
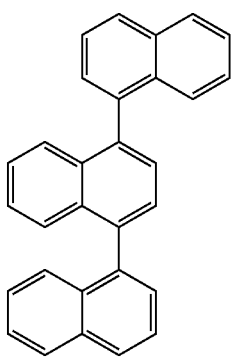 (66)

-continued
(67) 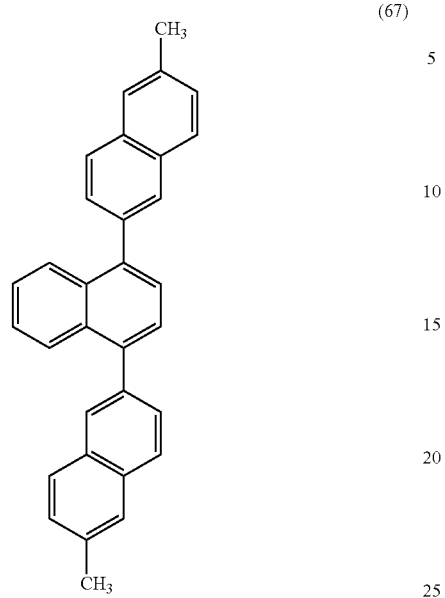
(68) 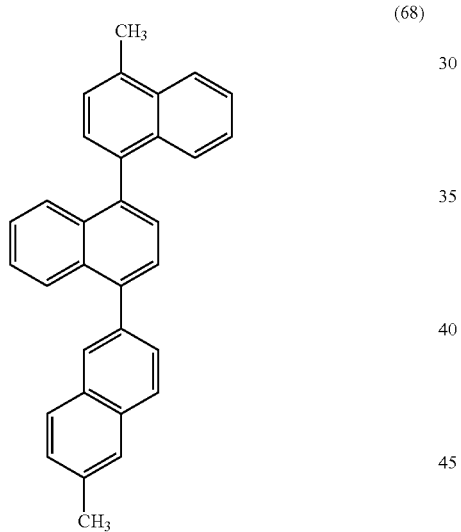
(69) 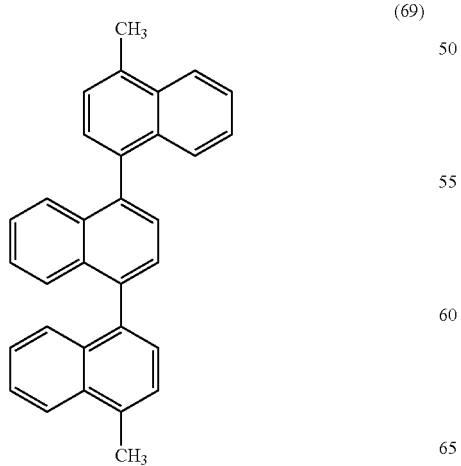
-continued
(70) 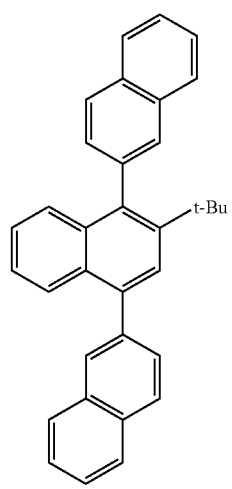
(71) 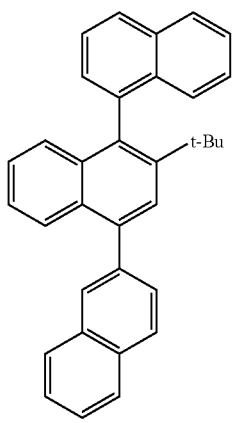
(72)

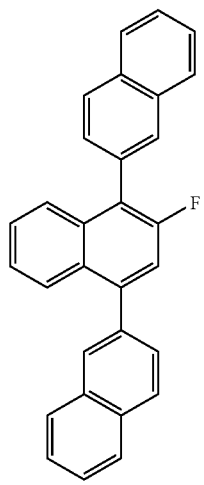
(73)
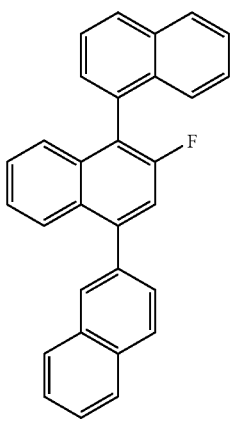
(74)
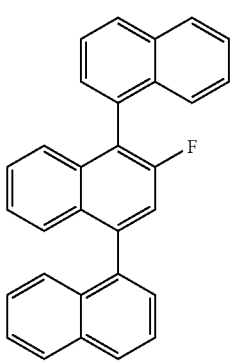
(75)
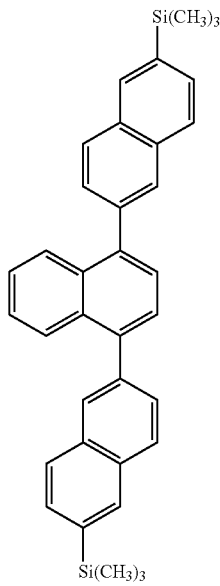
(76)
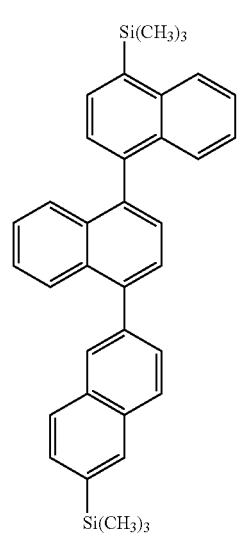
(77)
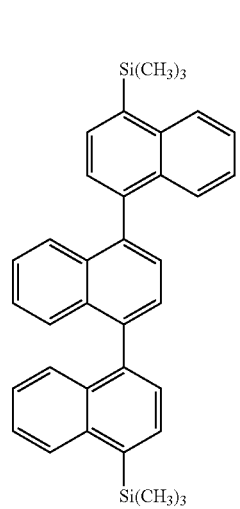
(78)

(79)
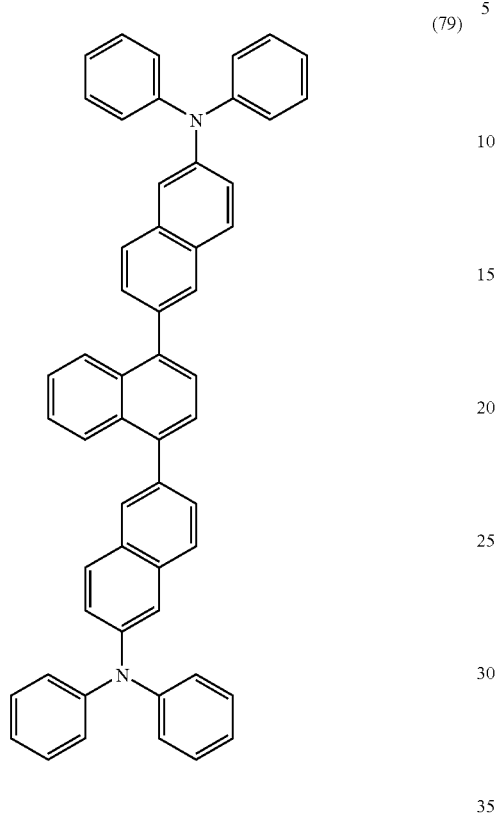
(80)
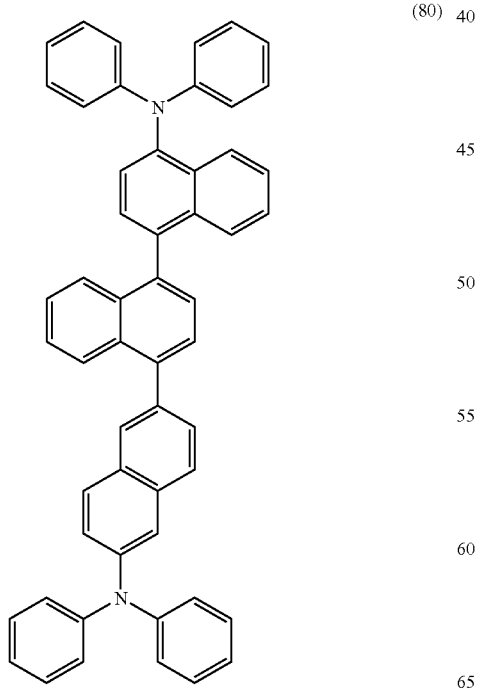
(81)
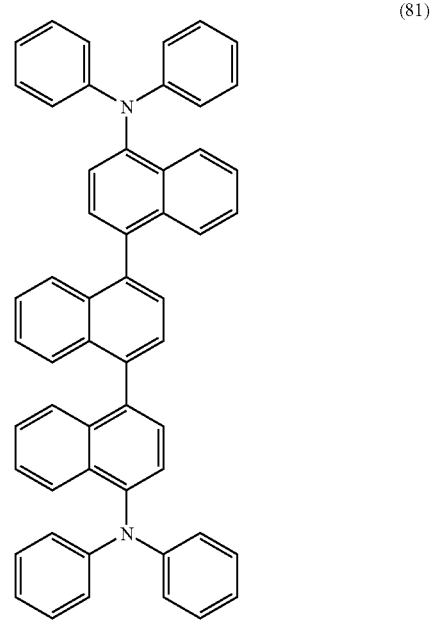
(82)
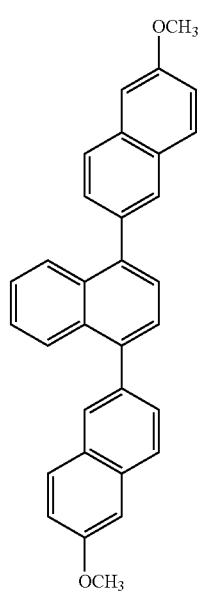

(83)
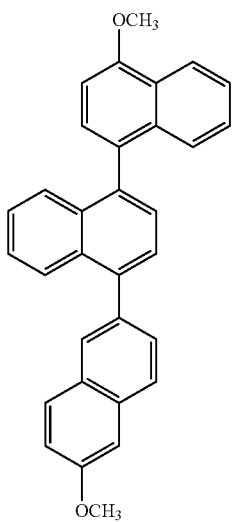
(84)
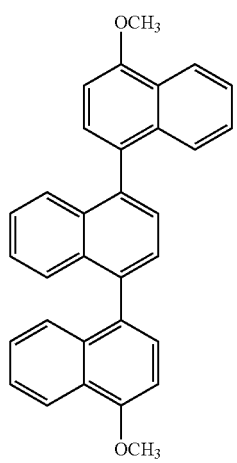
(85)
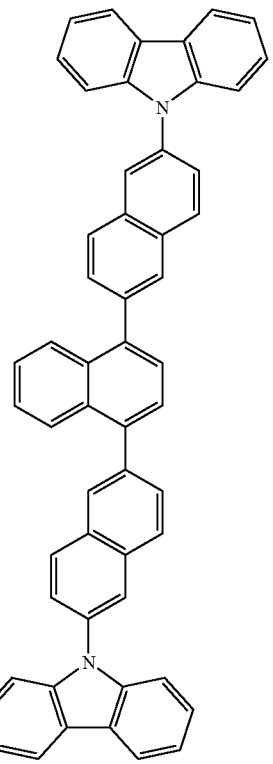
(86)
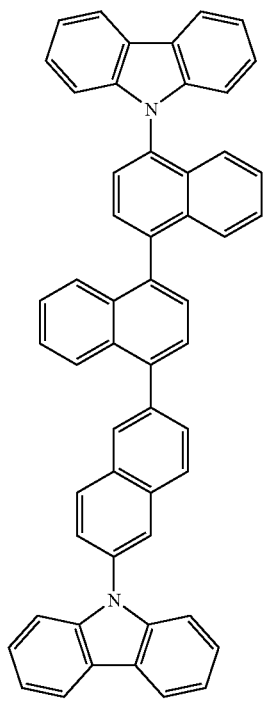

(87)
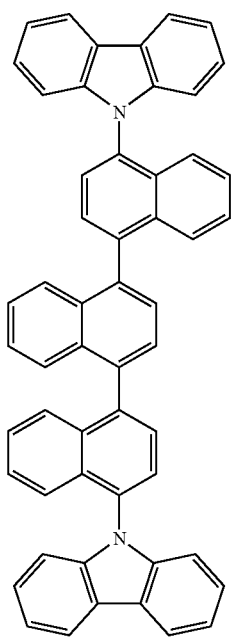
(88)
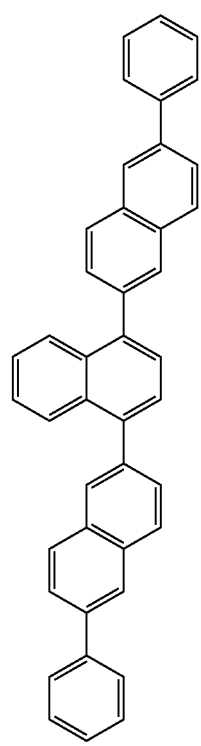
(89)
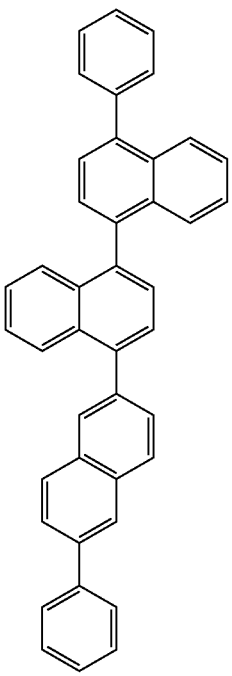
(90)
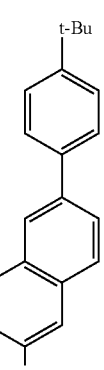
(91)

-continued
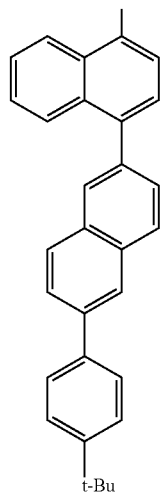
(92)
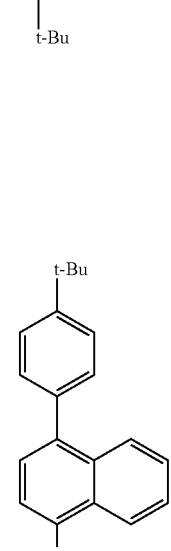
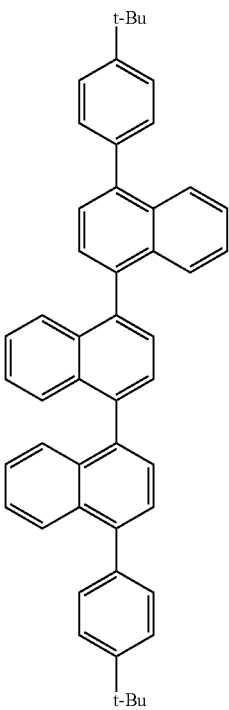
(93)
(94)
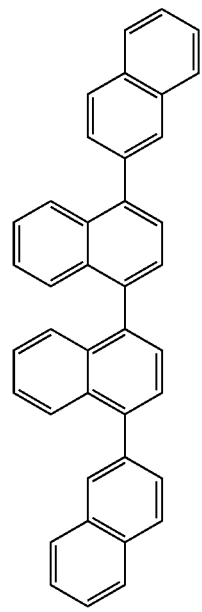

(95) 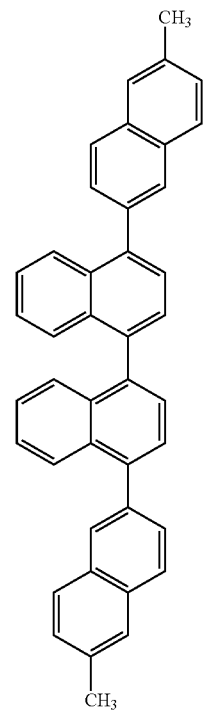
(96) 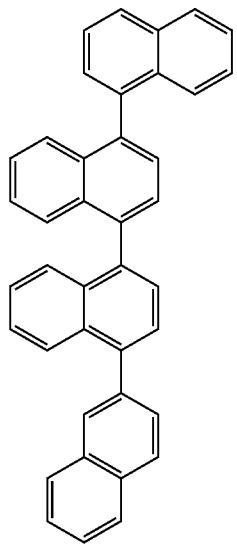
(97) 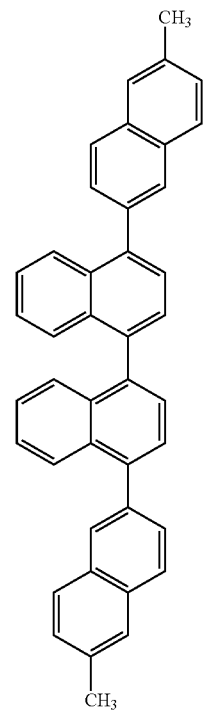
(98) 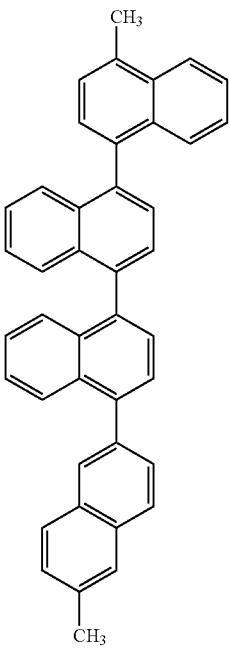

-continued
(99)
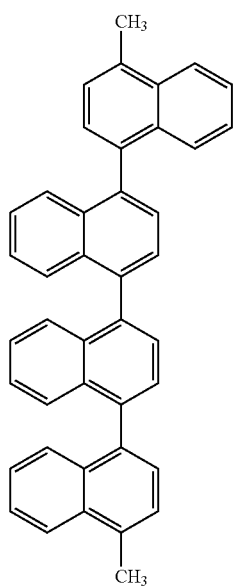
(100)
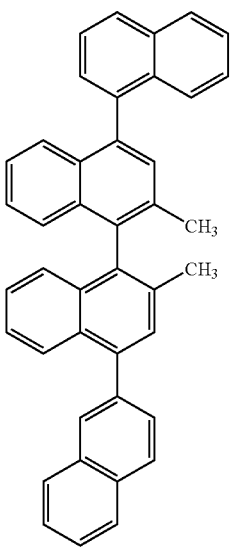
(101)
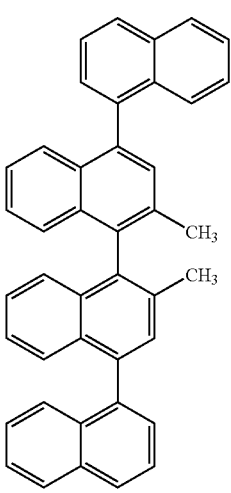
(102)
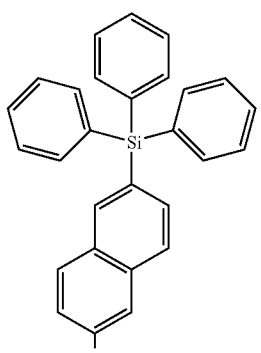
(103)

-continued
(104)
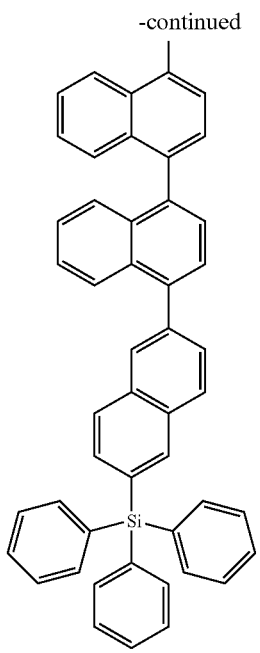
(105)
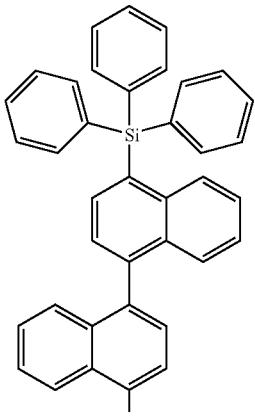
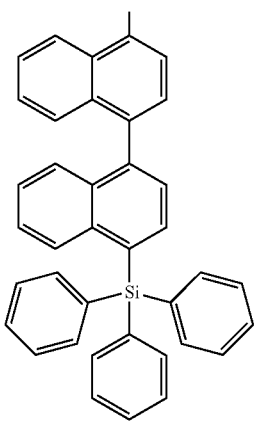
(106)
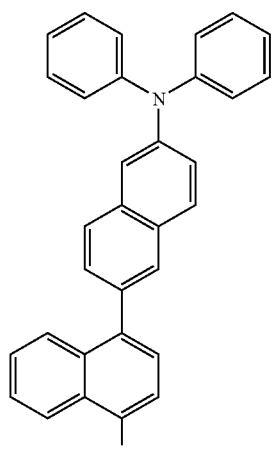

-continued
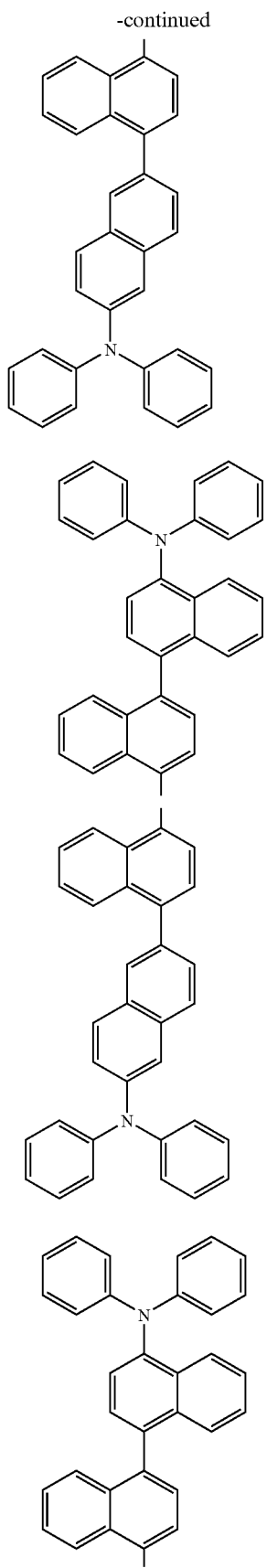
(107)
-continued
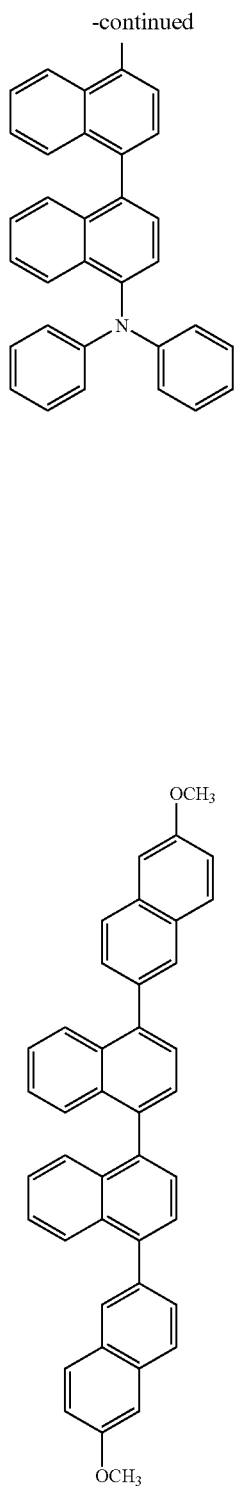
(109)
(108)

-continued
(110)
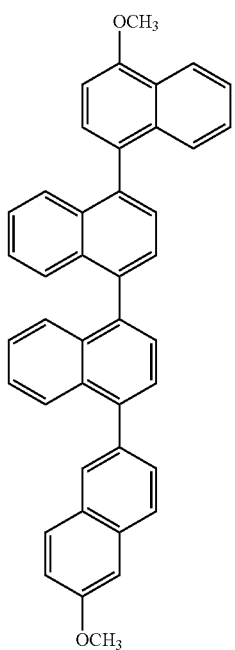
(111)
(112)
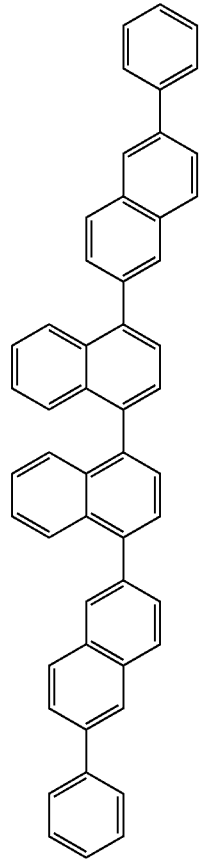
(113)
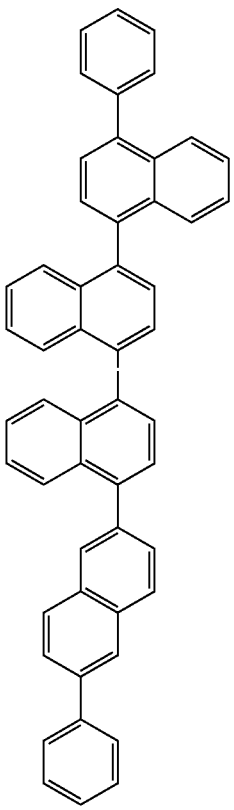

-continued
(114)
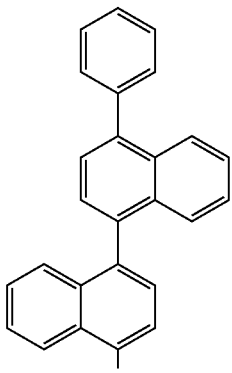
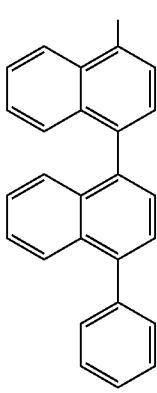
(115)
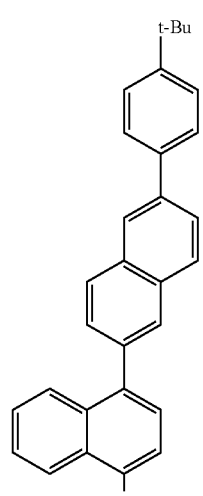
-continued
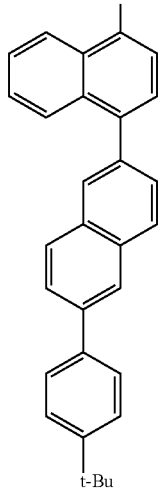
(116)
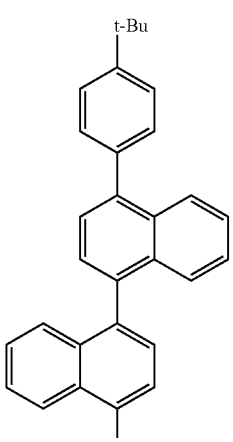
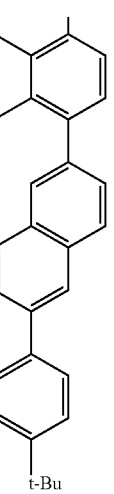

-continued
(117)
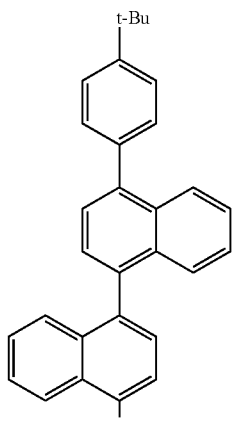
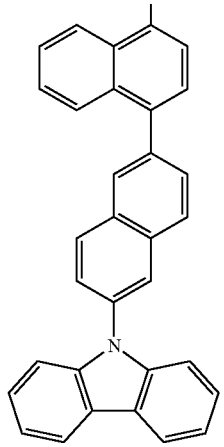
(118)
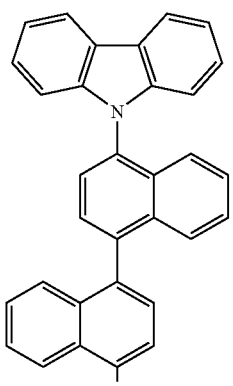
(119)
(120)
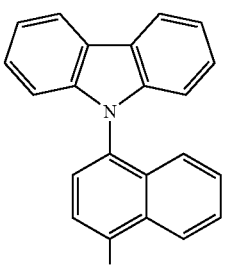

-continued
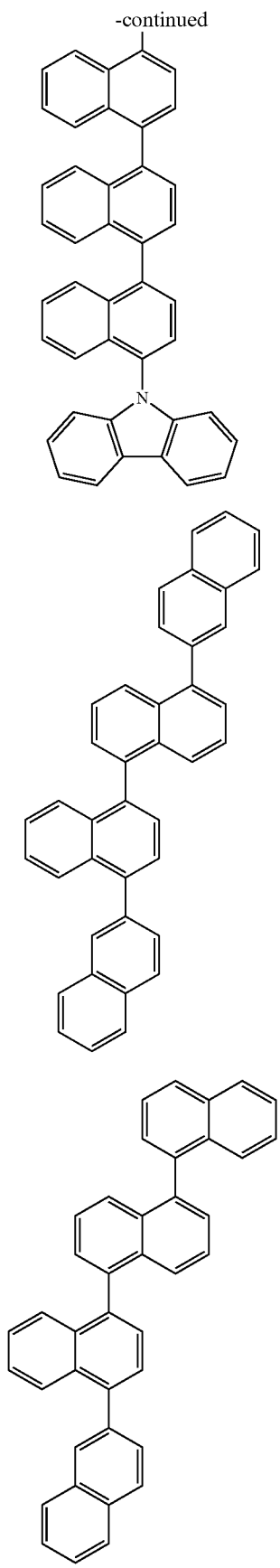
(121)
(122)
-continued
(123)
(124)
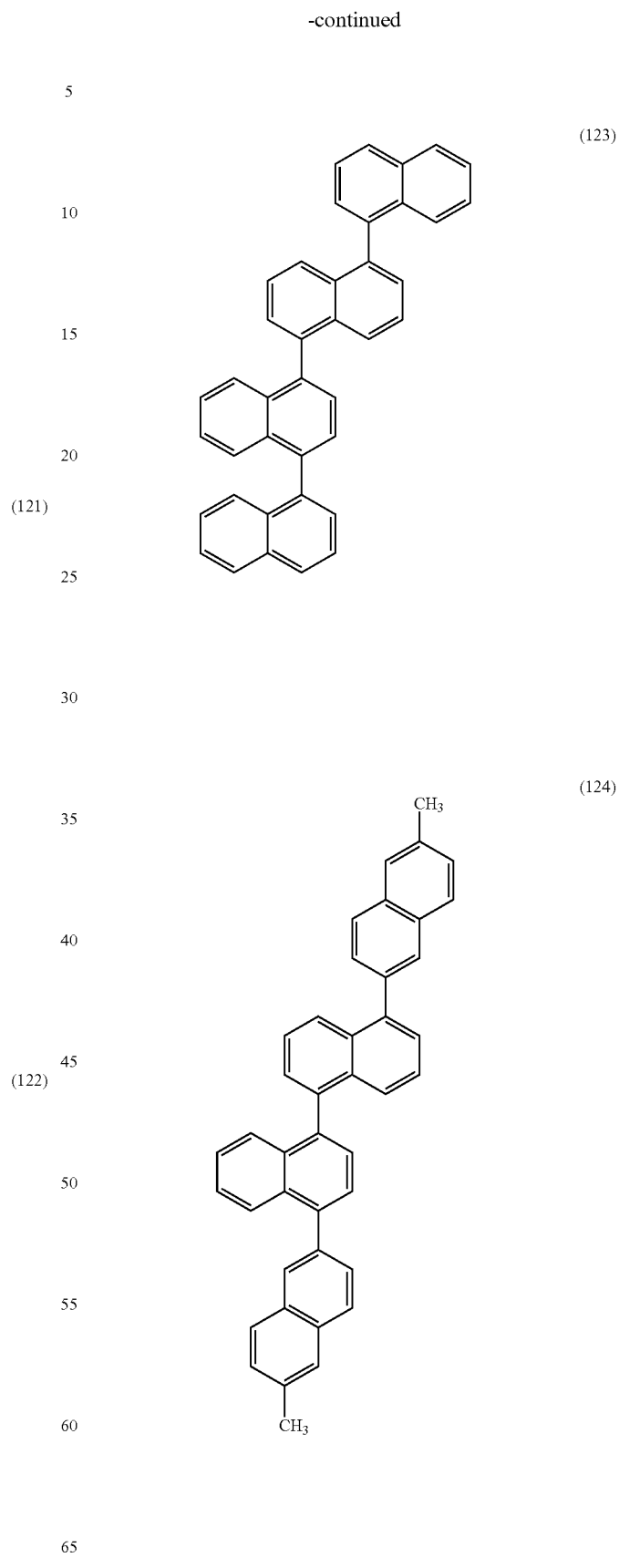

-continued
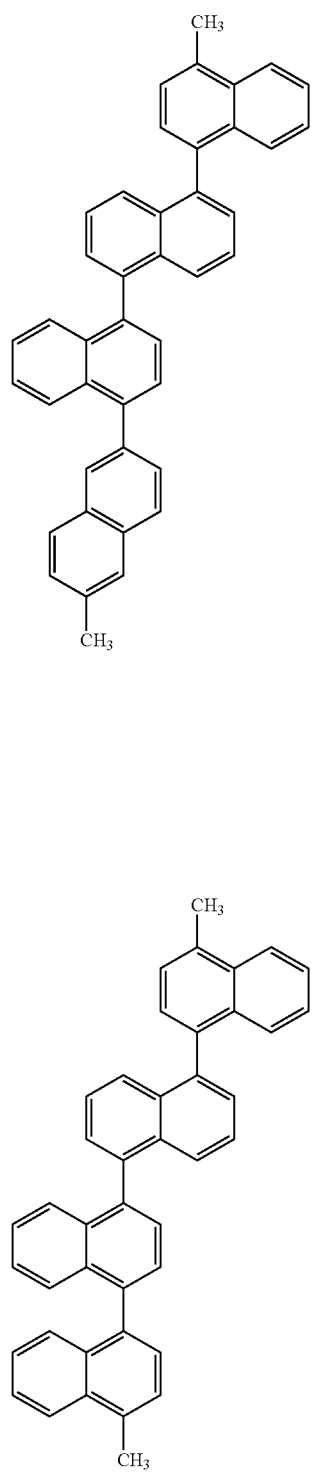
(125)
(126)
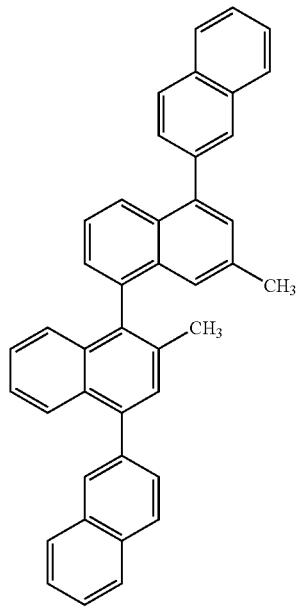
(127)
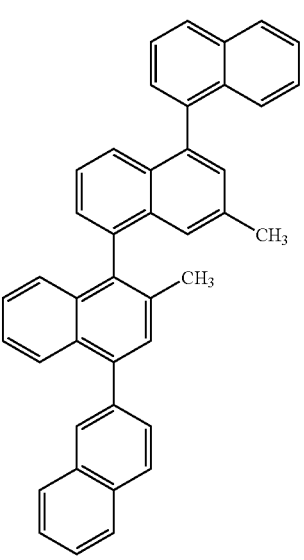
(128)
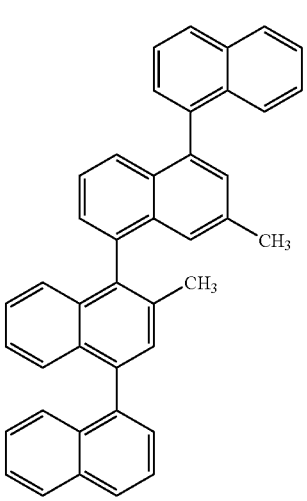
(129)

-continued
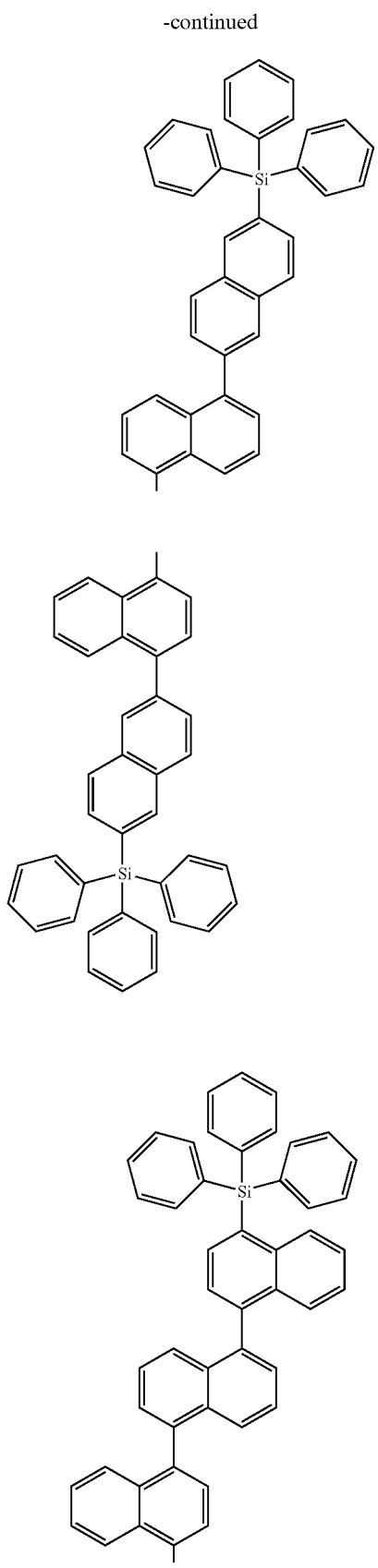
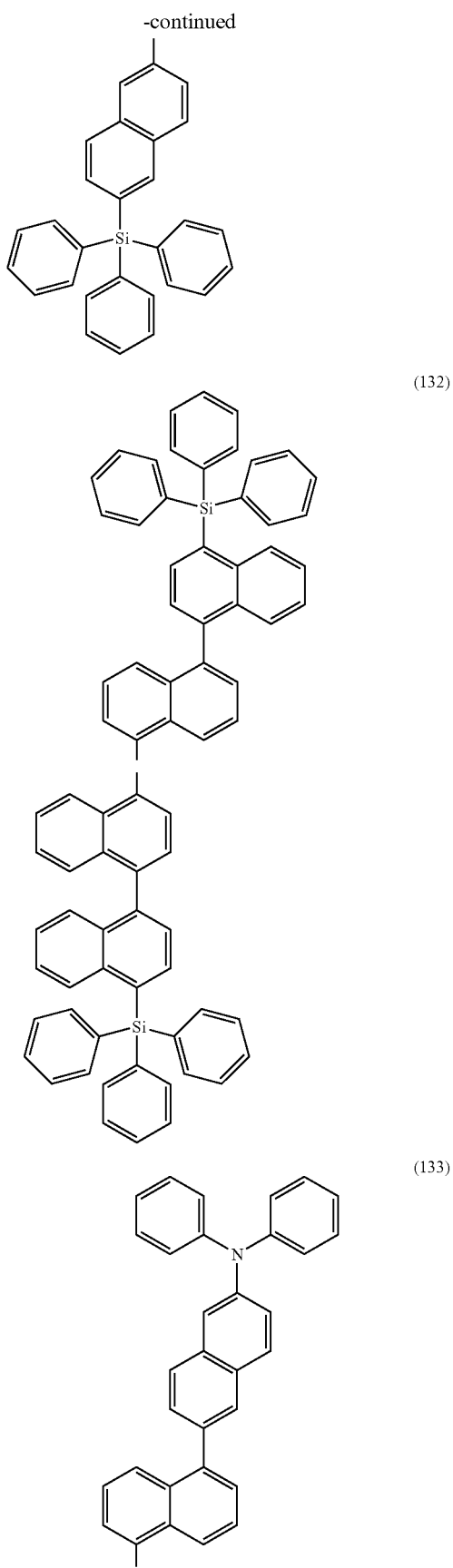

-continued
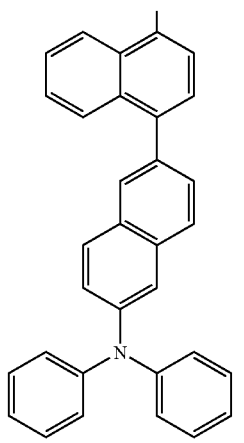
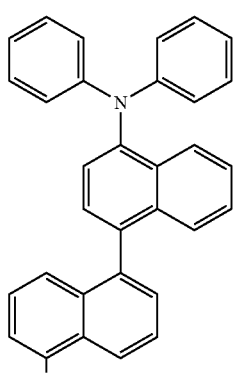
(134)
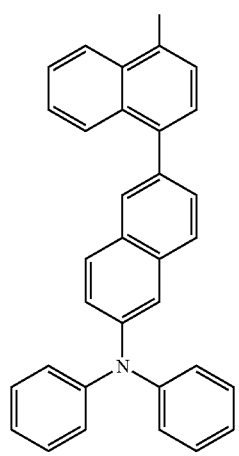
-continued
(135)
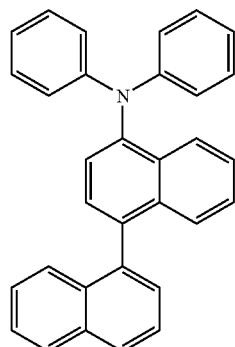
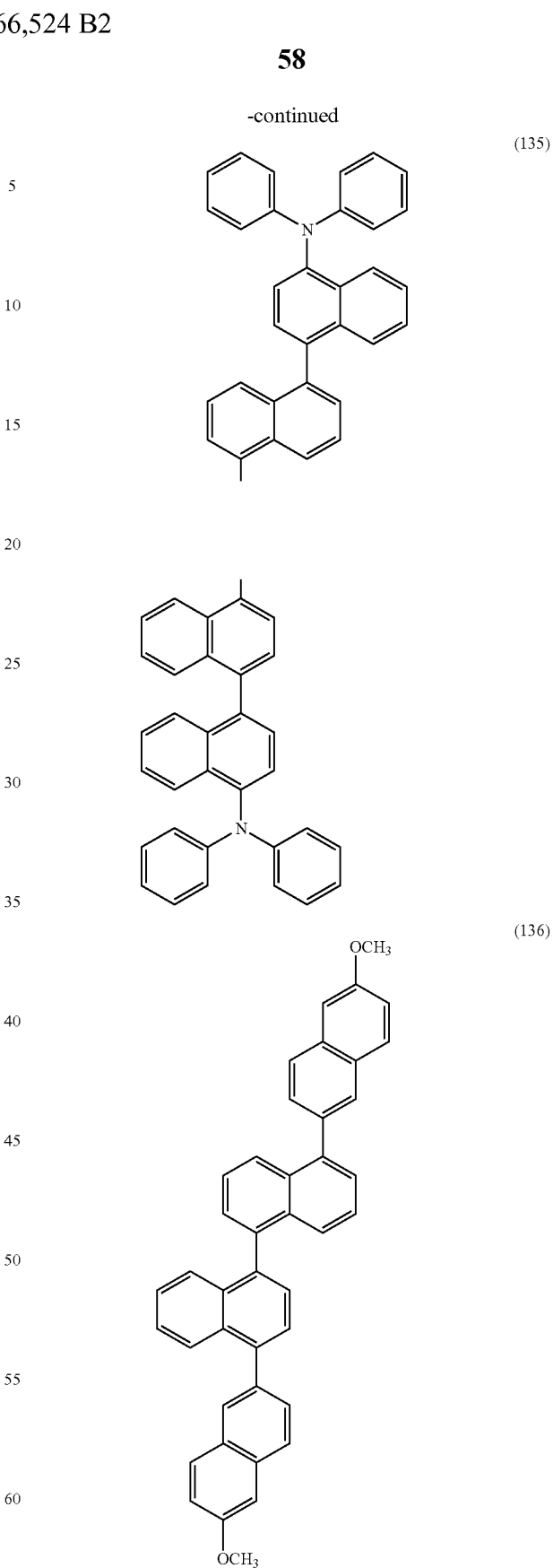
(136)
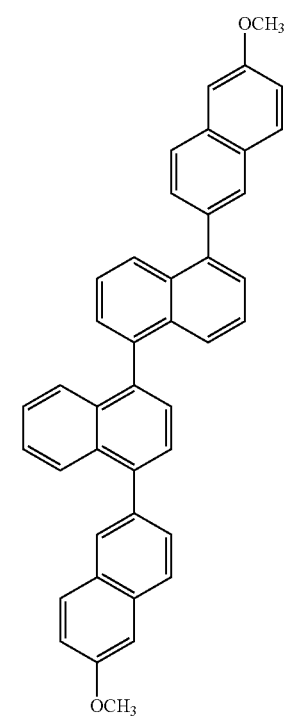

(137)
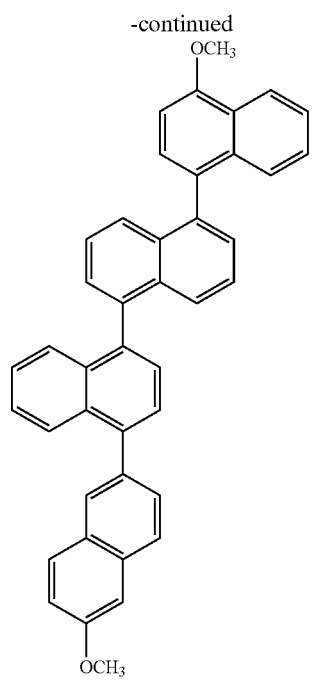
(138)
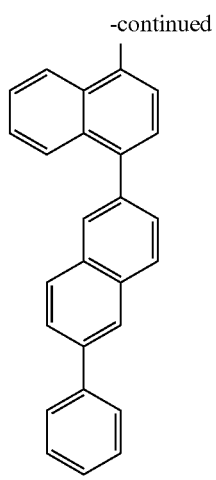
(139)
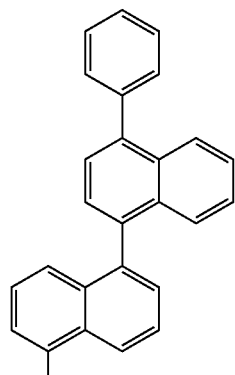
(140)
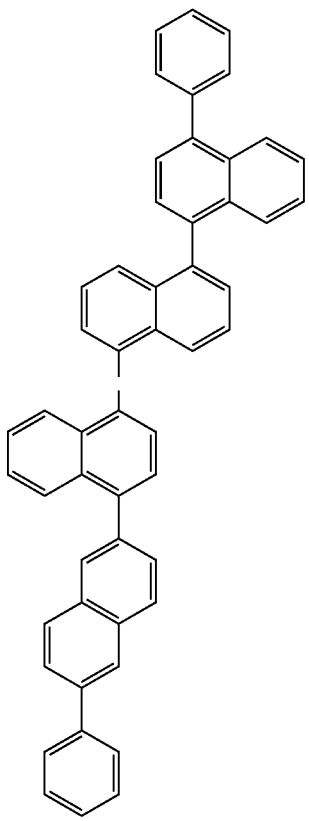
(141)

-continued
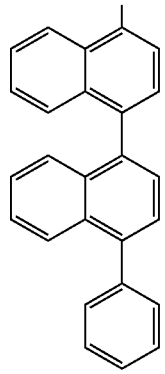
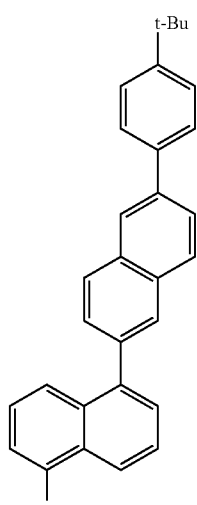
(142)
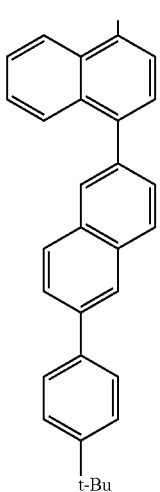
-continued
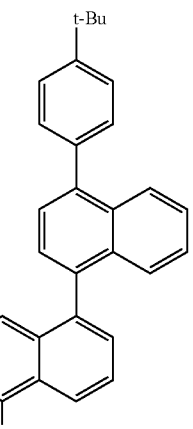
(143)
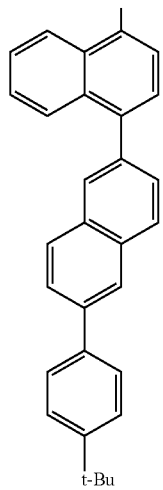
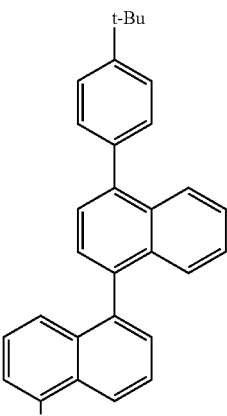
(144)

-continued

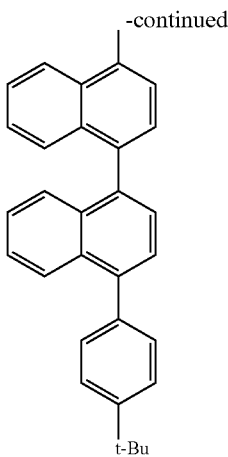

The oligonaphthalene derivative of the present invention has a feature that at least three naphthalene skeletons are sequentially bound.

The oligonaphthalene derivative of the present invention has an extremely large band gap; therefore, can emit light with extremely short wavelength, and can emit blue light with favorable color purity.

One feature of the above-described oligonaphthalene derivative of the present invention is that it has the maximum emission peak of 350 to 450 nm.

In addition, since the oligonaphthalene derivative of the present invention has a naphthalene skeleton that is a fused aromatic ring, it has a high carrier transporting property.

As a synthesizing method of the oligonaphthalene derivatives of the present invention, various reactions can be applied.

EMBODIMENT 2

Embodiment 2 describes a light-emitting element using an oligonaphthalene derivative of the present invention.

The structure of a light-emitting element of the present invention is a structure in which a layer including a luminescent material is formed between a pair of electrodes. The element structure is not limited, in particular, a known structure can be appropriately selected in accordance with a purpose.

FIG. 1 schematically shows the element structure of a light-emitting element according to the present invention as one example. The light-emitting element shown in FIG. 1 includes a layer including a luminescent material 102 between a first electrode 101 and a second electrode 103. The layer including a luminescent material 102 includes an oligonaphthalene derivative of the present invention. One of the first and second electrodes is an anode and the other is a cathode. The anode in the present invention indicates an electrode for injecting holes into the layer including a luminescent material. The cathode in the present invention indicates an electrode for injecting electrons into the layer including a luminescent material.

As the anode, known materials can be used; for example, a metal, an alloy, a conductive compound, and a mixture thereof each having a high work function (e.g., 4.0 eV or more) are preferably used. Specifically, indium tin oxide (also, referred to as ITO), indium tin oxide containing silicon, indium oxide containing zinc oxide (ZnO) of 2 to 20%, and the like are given. Such conductive metal oxide films are generally formed by sputtering; however, may be formed by a sol-gel method or the like. In addition, gold (Au), platinum (Pt), nickel (Ni), tungsten (W), chromium (Cr), molybdenum (Mo), iron (Fe), cobalt (Co), copper (Cu), palladium (Pd), or a nitride of a metal material (such as titanium nitride (TiN)) and the like can also be used.

As the cathode, known materials can be used; for example, a metal, an alloy, a conductive compound, and a mixture thereof each having a low work function (e.g., 3.8 eV or less) are preferably used. Specifically, a metal that belongs to Group 1 or 2 of the periodic table, namely, an alkali metal such as lithium (Li) and cesium (Cs); an alkaline earth metal such as magnesium (Mg), calcium (Ca) and strontium (Sr); an alloy containing the alkali metal or the alkaline earth metal (e.g., MgAg, AlLi); a rare earth metal such as europium (Eu) and ytterbium (Yb); and an alloy containing the rare earth metal, and the like can be given. However, a material having a high work function, namely, a material that is normally used for an anode, can be used to form the cathode by using the electron injecting layer having high electron injecting property. For example, the cathode can also be formed using a metal or a conductive inorganic compound such as Al, Ag and ITO.

As the layer including a luminescent material 102, known materials can be used; for example, any of low molecular weight materials and high molecular weight materials can be used. It is to be noted that the structure of materials for forming the layer including a luminescent material 102 include not only a structure containing only organic compounds but also a structure containing also an inorganic compound as a part thereof. In addition, the layer including a luminescent material may be formed by appropriately combining a hole injecting layer, a hole transporting layer, a hole blocking layer, a light-emitting layer, an electron transporting layer, an electron injecting layer, and the like. Further, the layer including a luminescent material may have a single layer structure or a stacked structure of plural layers.

The layer including a luminescent material can be formed by a wet type or dry type such as an evaporation method, an ink-jet method, a spin-coating method, or a dip-coating method.

The oligonaphthalene derivative of the present invention has an extremely large band gap, and can emit light with extremely short wavelength. Therefore, since the oligonaphthalene derivative of the present invention can emit blue light with favorable color purity, it can be used as a luminescent material of the light-emitting layer.

In addition, a luminescent material (dopant) having a band gap smaller than the oligonaphthalene derivative of the present invention is added into a layer including the oligonaphthalene derivative of the present invention to obtain a structure in which luminescence from the dopant can be obtained. At this time, since the oligonaphthalene derivative according to the present invention has an extremely large band gap, even if a dopant emitting light of a relatively short wavelength is used, luminescence from the dopant can be obtained efficiently instead of luminescence from the oligonaphthalene derivative. Specifically, a luminescent material having a maximum emission wavelength around 450 nm exhibits excellent color purity of blue, and such a material can be used as a dopant.

In the case where a dopant is added into a light-emitting layer including the oligonaphthalene derivative of the present invention to emit light from the dopant, any of a fluorescence luminescent material and a phosphorescence luminescent material can be used as the luminescent material to be added. Specifically, coumarin derivatives, oligophenylene derivatives, oxazole derivatives, stilbene derivatives, quinolone derivatives, acridone derivatives, anthracene derivatives, pyrene derivatives, phenanthrene derivatives and the like are preferred. The dopant is added in small amounts, specifically, at 0.001 to 50 wt %, preferably, 0.03 to 20 wt %.

Since the oligonaphthalene derivative of the present invention exhibits blue light emission with favorable color purity, it may be used as a dopant for light emission. When the oligonaphthalene derivative of the present invention is used as the dopant for light emission, tetraaryl silane derivatives, benzophenone derivatives, benzonitrile derivatives and the like can be used as a host material forming the light-emitting layer.

In addition to the light-emitting layer, layers formed using different materials may be stacked on cathode and anode sides of the light-emitting layer. Specifically, decrease of driving voltage of the light-emitting element can be achieved by arranging an electron injecting layer and a hole injecting layer promoting carrier injection from electrodes between the light-emitting layer and the cathode, and between the light-emitting layer and the anode, respectively.

As a hole injecting material that forms a hole injecting layer, known materials can be used. Specifically, metal oxides such as vanadium oxide, molybdenum oxide, ruthenium oxide and aluminum oxide are preferable. In addition, a porphyrin compound among organic compounds is effective, and phthalocyanine ($H_2$-Pc), copper phthalocyanine (Cu-Pc), and the like can also be used. Further, a material that is obtained by chemical doping to a conductive high molecular weight compound, for example, polyethylene dioxythiophene (PEDOT) doped with polystyrene sulfonate (PSS), polyaniline (PAni) and the like can be used.

As an electron injecting material that forms an electron injecting layer, known materials can be used. Specifically, alkali metal salts or alkaline earth metal salts such as calcium fluoride, lithium fluoride, lithium oxide, lithium chloride are preferred. A layer in which a compound with donating property such as lithium is added into a material having electron transporting property, e.g., tris(8-quinolinolato) aluminum (Alq3) or bathocuproine (BCP) can also be used.

A carrier injection barrier is lowered and carriers are injected into a light-emitting element efficiently by using such electron and hole injecting layers. As a result, decrease in the driving voltage can be achieved.

A carrier transporting layer is preferably formed between a carrier injecting layer and the light-emitting layer. This is because a portion of light emitted from the light-emitting layer is quenched and thus, emission efficiency is decreased, when the carrier injecting layer is in contact with the light-emitting layer. In the case of using the hole transporting layer, the hole transporting layer is arranged between the hole injecting layer and the light-emitting layer. As a preferred material, an aromatic amine based compound (i.e., one having a bond of a benzene ring and nitrogen) is given. As the material widely used, a star burst aromatic amine compound such as 4,4'-bis[N-(3-methylphenyl)-N-phenyl-amino]-biphenyl; or derivatives thereof, e.g., 4,4'-bis[N-(1-naphthyl)-N-phenyl-amino]-biphenyl; 4,4',4''-tris(N,N-diphenyl-amino)-triphenylamine; 4,4',4''-tris[N-(3-methylphenyl)-N-phenyl-amino]-triphenylamine can be given.

In the case of using an electron transporting layer, the electron transporting layer is arranged between the light-emitting layer and an electron injecting layer. As a suitable material, typical metal complexes such as tris(8-quinolinolato) aluminum ($Alq_3$), tris(4-methyl-8-quinolinolato) aluminum ($Almq_3$), bis(10-hydroxybenzo [h]-quinolinato)beryllium ($BeBq_2$), or bis(2-methyl-8-quinolinolato)-(4-hydroxy-biphenyly)-aluminium (BAlq), bis[2-(2-hydroxyphenyl)-benzoxazolato] zinc ($Zn(BOX)_2$), bis[2-(2-hydroxyphenyl)-benzothiazolato]zinc (Zn(BTZ)2) can be given. In addition, hydrocarbon based compounds such as 9,10-diphenylanthracene or 4,4'-bis(2,2-diphenyl ethenyl) biphenyl are preferred. Further, triazole derivatives such as 3-(4-tert-buthylphenyl)-4-(4-ethylphenyl)-5-(4-biphenylyl)-1,2,4-triazole, or phenanthroline derivatives such as bathophenanthroline and bathocuproine may be used.

In this embodiment, a dopant for light-emission is added into only the light-emitting layer, and the luminescence from the dopant is observed. However, a dopant for different light-emission may be added into a different layer, e.g., an electron transporting layer or a hole transporting layer. As to the dopant at this time, in addition to the fluorescent luminescent material such as a coumarin derivative, a quinacridon derivative, an acridone derivative, a pyrene derivative, a perylene derivative, an anthracene derivative, a pyrone derivative, a phosphorescence luminescent material such as tris (2-phenylpyridine) iridium ($Ir(ppy)_3$) and 2,3,7,8,12,13,17,18-octa-ethyl-21H,23H-porphyrin-platinum (PtOEP), Ir, Ru, Ph, Pt or a rare earth metal may be used. When light emitted from the light-emitting layer has a relation of complementary color with respect to light emitted from the dopant added in the different layer mentioned above, white light is obtained.

The oligonaphthalene derivative of the present invention has an extremely large band gap; therefore, a light-emitting element using the oligonaphthalene derivative of the present invention can emit light with extremely short wavelength, and can emit blue light with favorable color purity.

By using oligonaphthalene derivative of the present invention as a luminescent material of a light-emitting element, a light-emitting element that can exhibit excellent color purity of blue can be provided.

In addition, a luminescent material having a band gap smaller than the oligonaphthalene derivative of the present invention is added into a layer including the oligonaphthalene derivative of the present invention to obtain luminescence from the dopant. At this time, since the oligonaphthalene derivative of the present invention has an extremely large band gap, even if a dopant emitting light of a relatively short wavelength is used, luminescence from the dopant can be obtained efficiently instead of luminescence from the oligonaphthalene derivative of the present invention. Accordingly, blue light emission with excellent color purity can be obtained.

In addition, since the above described oligonaphthalene derivative of the present invention has a naphthalene skeleton that is a fused aromatic ring, it has a high carrier transporting property. Therefore, the oligonaphthalene derivative of the present invention may be used as a carrier transporting layer of the layer including a luminescent material.

EMBODIMENT 3

Embodiment 3 describes a light-emitting device having a light-emitting element of the present invention.

This embodiment describes a light-emitting device having a light-emitting element of the present invention in its pixel portion with reference to FIGS. 11A and 11B. FIG. 11A is a top view of the light-emitting device, while FIG. 11B is a cross-sectional view taken along A-A' and B-B' in FIG. 11A. Reference numeral 601 shown by a dotted line denotes a driver circuit (source side driver circuit); 602, a pixel portion; 603, a driver circuit portion (gate side driver circuit); 604, a sealing substrate; 605, a sealing material; and 607, a space surrounded by the sealing material 605.

Reference numeral 608 denotes a leading wiring for transmitting signals to be inputted into the source side driver circuit 601 and the gate side driver circuit 603 and receiving signals such as a video signal, a clock signal, a start signal, and a reset signal from an FPC (flexible printed circuit) 609 serving as an external input terminal. Although only the FPC is illustrated here, a print wiring board (PWB) may be attached to this FPC and the light-emitting device in this specification may include not only the light-emitting device itself but also the light-emitting device with the FPC and/or the PWB attached thereto.

Next, the cross-sectional structure is described with reference to FIG. 11B. The driver circuit portion and the pixel portion are formed over an element substrate 610. In this embodiment, the source side driver circuit 601, which is the driver circuit portion, and one pixel of the pixel portion 602 are shown.

In the source side driver circuit 601, a CMOS circuit is formed in which an n-channel TFT 623 and a p-channel TFT 624 are combined. Further, the driver circuit may be formed with a known CMOS circuit, PMOS circuit, or NMOS circuit using TFTs. Although this embodiment shows an example of forming the pixel portion and the driver circuit formed over the same substrate, the present invention is not limited to this, and the driver circuit can also be formed outside, not over the same substrate as the pixel portion.

The pixel portion 602 is formed with a plurality of pixels including a switching TFT 611, a current controlling TFT 612, and a first electrode 613 connected electrically with a drain region of the current controlling TFT. An insulator 614 is formed so as to cover the end portions of the first electrode 613. Here, a positive photosensitive acrylic resin film is used as the insulator 614.

In order to improve the coverage, the insulator 614 is formed so as to have a curved surface with curvature at its upper or lower end portion. For example, in the case of using positive photosensitive acrylic for the insulator 614, only the upper end portion of the insulator 614 preferably has a curved surface with a radius of curvature of 0.2 to 0.3 μm. The insulator 614 may be formed with either a negative type, which becomes insoluble to the etchant by the irradiation of light, or a positive type, which becomes soluble to the etchant by the irradiation of light.

A layer including a luminescent material 616 and a second electrode 617 are formed over the first electrode 613. The first electrode 613 serving as an anode is preferably formed with a material having a high work function. For example, a single layer of an indium tin oxide (ITO) film, an indium tin oxide film containing silicon, an indium tin oxide film containing zinc oxide (ZnO) of 2 to 20%, a titanium nitride film, a chromium film, a tungsten film, a Zn film, a Pt film, a stacked layer of a titanium nitride film and a film mainly containing aluminum, a three-layer stacked structure of a titanium nitride film, a film mainly containing aluminum and a titanium nitride film, and the like can be used. Note that, when a stacked structure is employed, resistance of a wiring is low and a favorable ohmic contact is obtained, and thus the stacked structure can function as an anode.

The layer including the luminescent material 616 is formed by a method such as evaporation, ink jet, spin coating, or dip coating. The layer including a luminescent material 616 includes an oligonaphthalene derivative of the present invention. In addition, a low molecular weight material, a middle molecular weight material (including oligomer and dendrimer), or a high molecular weight material may be used as a material which is combined with the oligonaphthalene derivative of the present invention. Further, as a material used for the layer including a luminescent material, in many cases, an organic compound is used as a single layer or a multilayer; however, a structure in which an inorganic compound is used in a part of a film including an organic compound is included in the present invention.

Since the oligonaphthalene derivative of the present invention has excellent color purity of blue, blue light with favorable color purity can be obtained by using the oligonaphthalene derivative of the present invention as a luminescent material. Thus, a light-emitting device using a light-emitting element of the present invention provides superior color reproducibility.

Since the oligonaphthalene derivative of the present invention has an extremely large band gap, it can be used as a host material constituting a part of the light-emitting layer. In addition, since the oligonaphthalene derivative of the present invention has an extremely large band gap, even if a dopant emitting light of a relatively short wavelength is used, luminescence from the dopant can be obtained efficiently instead of luminescence from the oligonaphthalene derivative of the present invention.

As the material for the second electrode (cathode) 617 formed over the layer including a luminescent material 616, a material having a low work function is preferable. For example, Al, Mg, Li, Ca, an alloy or compound such as MgAg, MgIn, AlLi, $CaF_2$ or a calcium nitride or the like can be used. When light generated in the layer including a luminescent material 616 passes through the second electrode 617, a stacked layer of a thin metal film having a thin thickness, and a transparent conductive film (such as ITO, indium oxide including zinc oxide of 2 to 20%, indium tin oxide including silicon, zinc oxide (Zno) or the like) can be used as the second electrode (cathode) 617.

Further, a light-emitting element 618 is right beside the space 607 surrounded by the element substrate 610, the sealing substrate 604, and the sealing material 605 by pasting the sealing substrate 604 and the element substrate 610 using the sealing material 605. The space 607 may be filled with an inert gas such as nitrogen or argon, or the sealing material 605.

An epoxy based resin is preferably used for the sealing material 605. It is preferable that these materials do not transmit oxygen or moisture as much as possible. As the material for the sealing substrate 604, a glass substrate, a quartz substrate, a plastic substrate made of FRP (Fiberglass-Reinforced Plastics), PVF (polyvinyl fluoride), mylar, polyester, acrylic, or the like can be used.

As thus described, a light-emitting device having a light-emitting element of the present invention can be obtained.

EXAMPLE 1

In Example 1, a synthesizing method of a compound shown by formula (94), i.e., 4,4'-bis(2-naphthyl)-1,1'-binaphthyl (DNBN2) as one example of a material according to the present invention is descrived.

(94)

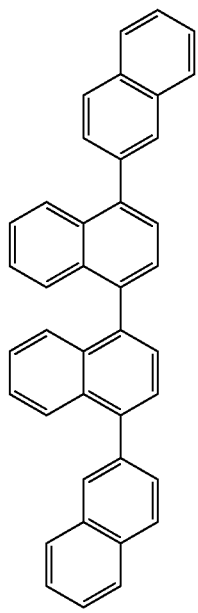

Synthesis scheme of 4,4'-bis(2-naphthyl)-1,1'-binaphthyl (DNBN2) is shown by (A-1).

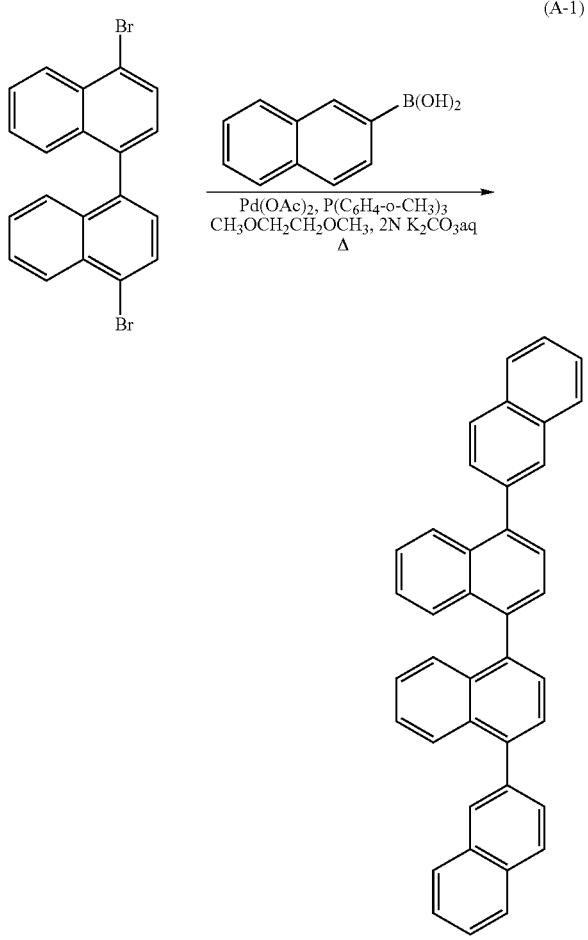

(A-1)

Figure 5:
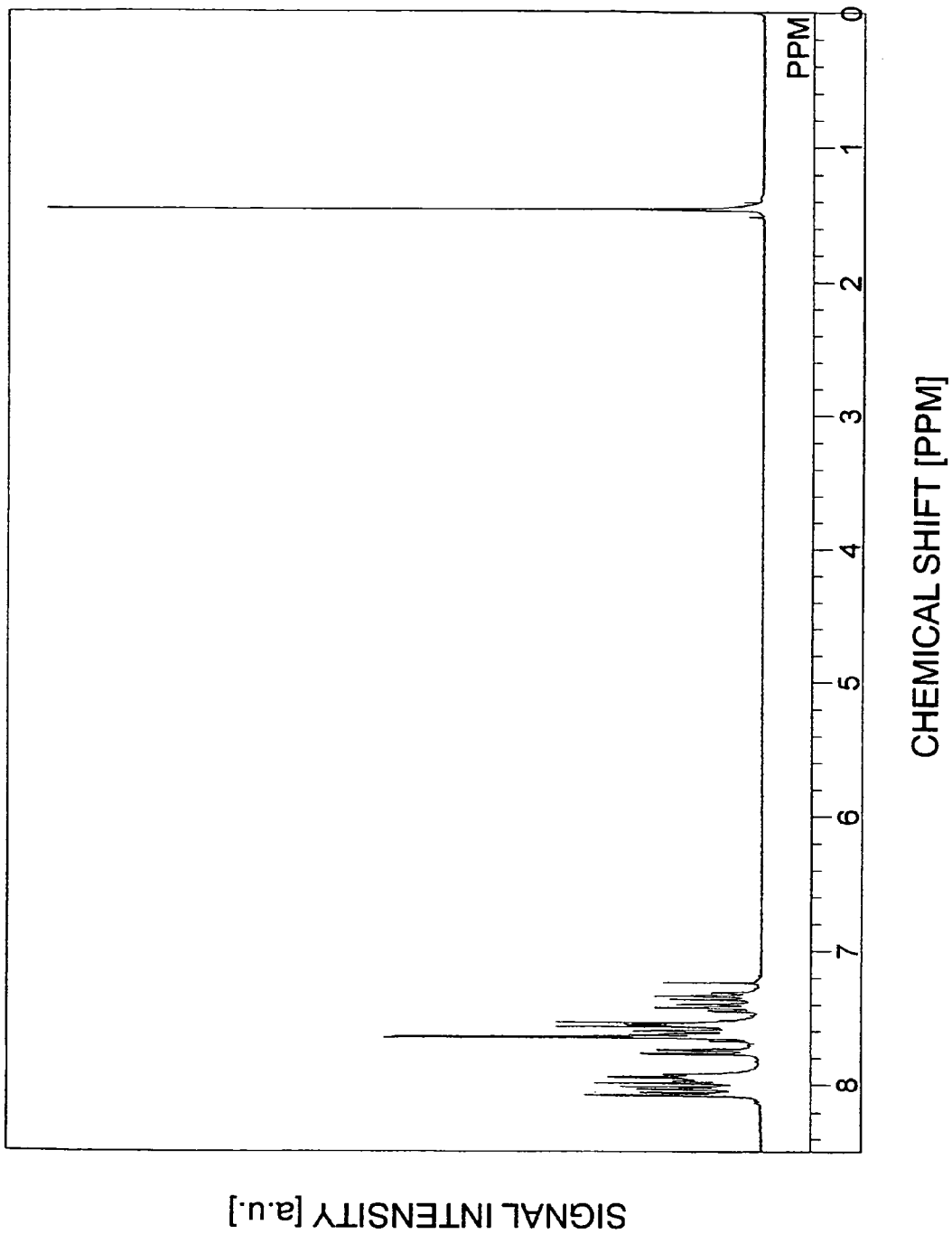
FIG. 5 shows ¹H NMR chart of 4,4'-bis(2-naphthyl)-1,1'-binaphthyl that is an oligonaphthalene derivative according to one aspect of the present invention.
Figure 6:
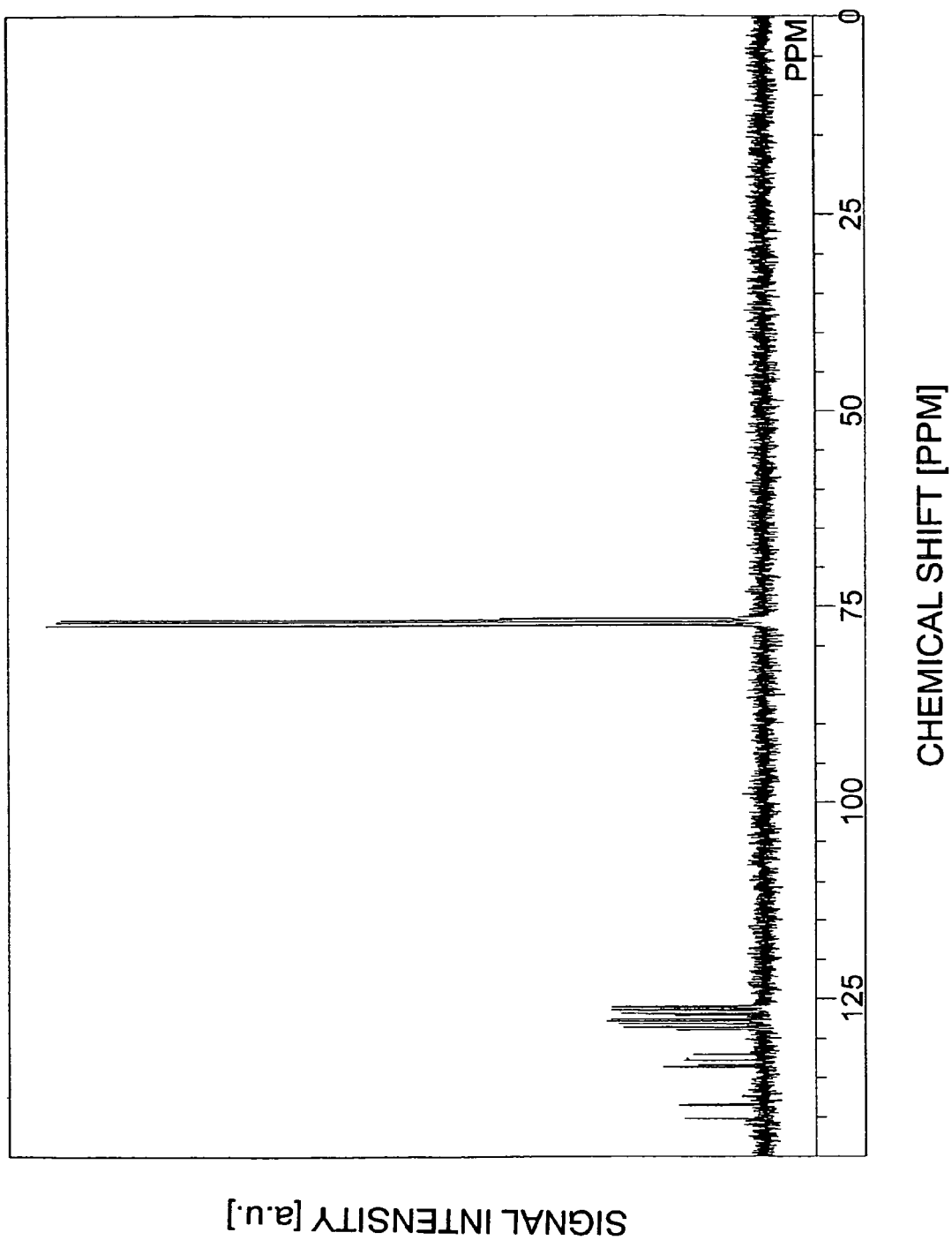
FIG. 6 shows ¹³C NMR chart of 4,4'-bis(2-naphthyl)-1,1'-binaphthyl that is an oligonaphthalene derivative according to one aspect of the present invention.

4,4'-dibromo-1,1'-binaphthyl (1.65 g, 4 mmol), 2-naphthyl boronic acid (1.72 g, 10 mmol), palladium acetate (89 mg, 0.4 mmol), and tris(2-methylphenyl)phosphine (910 mg, 3 mmol) were suspended in 90 mL of ethylene glycol dimethyl ether. 7.2 mL of 2N-potassium carbonate solution was added to this suspension, and was stirred at 90° C. for four and half hours. The reaction mixture was filtered and a solid matter obtained by the filtration was washed with methanol. This solid matter was suspended in about 200 mL of chloroform and was filtered to obtain a filtrate. The filtrate was concentrated, ethyl acetate was added and ultrasonic wave was applied thereto, thereby obtaining precipitation of a compound (DNBN2). The precipitated DNBN2 was obtained by filtering (1.5 g, yield 74%). Purification was conducted by sublimation. NMP data is shown below. $^1$H NMR (300 MHz, CDCl$_3$); δ=7.31-7.37 (m, 2H), 7.40-7.45 (m, 2H), 7.54-7.67 (m, 10H), 7.74-7.77 (m, 2H), 7.92-8.08 (m, 10H): $^{13}$C NMR (75 MHz, CDCl$_3$); δ=125.9, 126.0, 126.1, 126.4, 126.5, 126.8, 127.1, 127.6, 127.8, 127.8, 128.2, 128.6, 129.0, 132.1, 132.8, 133.4, 133.6, 138.4, 138.5, 140.2. FIG. 5 and FIG. 6 show obtained charts of $^1$H NMR and $^{13}$C NMR of DNBN2, respectively.

DNBN2 was a white powder and thermogravimetry-differential thermal analysis (TG-DTA) of the obtained DNBN2 was conducted. Note that a thermogravimetry-differential thermal analysis apparatus (TG/DTA 320 manufactured by Seiko Instruments Inc.) was used to measure the DNBN2. Thermophysical properties were evaluated under a nitrogen atmosphere with a rising temperature of 10° C./min. Consequently, the temperature at which the weight was 95% or less of the weight at the starting point of the measurement was 365° C.

Figure 2:
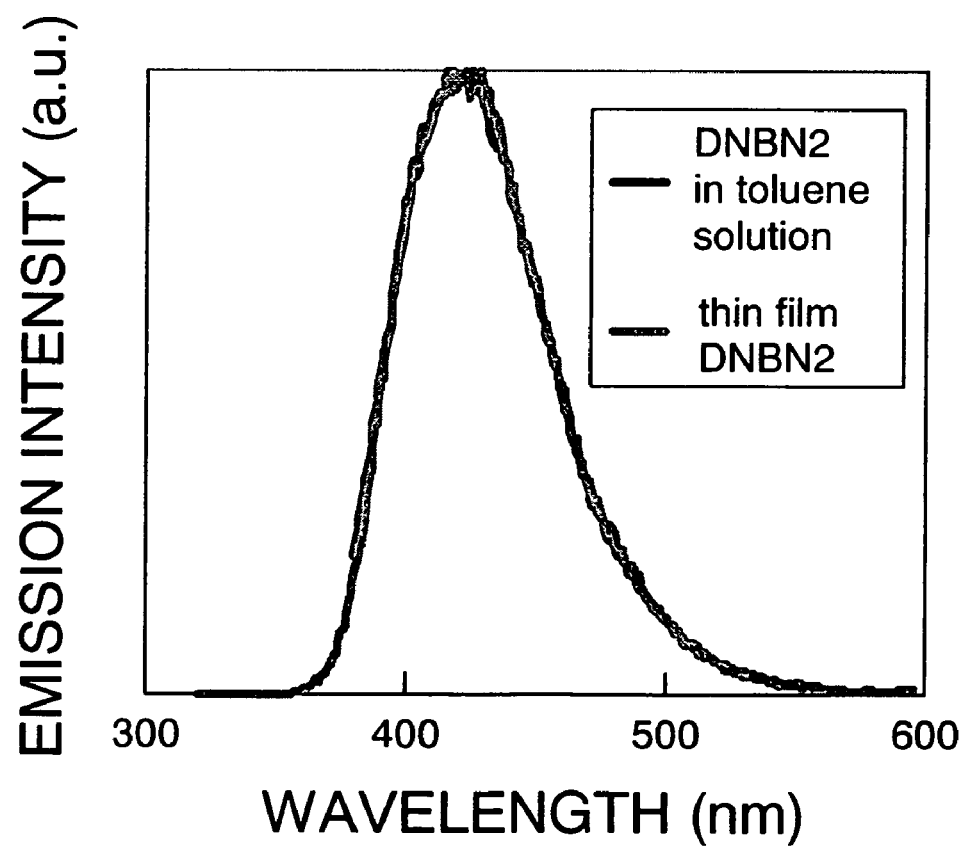
FIG. 2 shows an emission spectrum of 4,4'-bis(2-naphthyl)-1,1'-binaphthyl that is an oligonaphthalene derivative according to one aspect of the present invention.

An absorption spectrum of toluene solution of DNBN2 and a thin film state of DNBN2 were measured. The maximum absorption wavelength of toluene solution of DNBN2 and thin film state of DNBN2 were 310 nm and 320 nm, respectively. In addition, FIG. 2 shows emission spectra of toluene solution of DNBN2 and the thin film state of DNBN2. In FIG. 2, the horizontal axis indicates a wavelength (nm) and the vertical axis indicates emission intensity (arbitrary unit). It can be found that the maximum emission wavelength of toluene solution and the thin film state of DNBN2 were 420 nm (excitation wavelength 330 nm) and 428 nm (excitation wavelength 300 nm), respectively, and thus, light in a short wavelength can be obtained.

HOMO level and LUMO level in the thin film state of DNBN2 were measured. The value of HOMO level was obtained by converting a value of the ionization potential measured with a photoelectron spectroscopy device (AC-2 manufactured by Riken Keiki Co., Ltd) to a negative value. The value of LUMO level was obtained by adding an energy gap between absorption edges of the thin film state to a value of HOMO level. As a result, HOMO level and LUMO level were −5.83 eV and −2.53 eV, respectively and thus the extremely large band gap of 3.3 eV was obtained.

EXAMPLE 2

In Example 2, a synthesizing method of a compound shown by structural formula (34), i.e., 1,5-di(2-naphthyl) naphthalene (DNN1) as one example of a material according to the present invention is described.

(34)

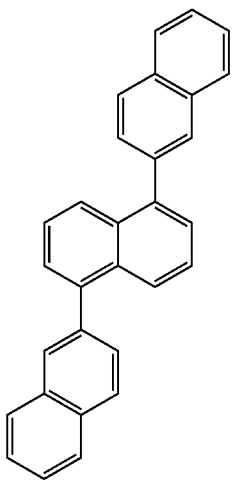

Synthesis scheme of 1,5-di(2-naphthyl)naphthalene (DNN1) is shown by (A-2).

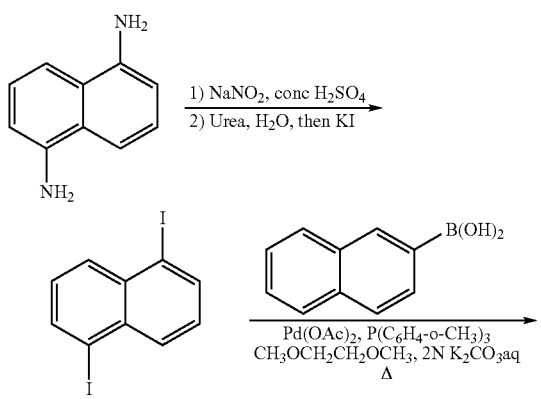
(A-2)

Figure 7:
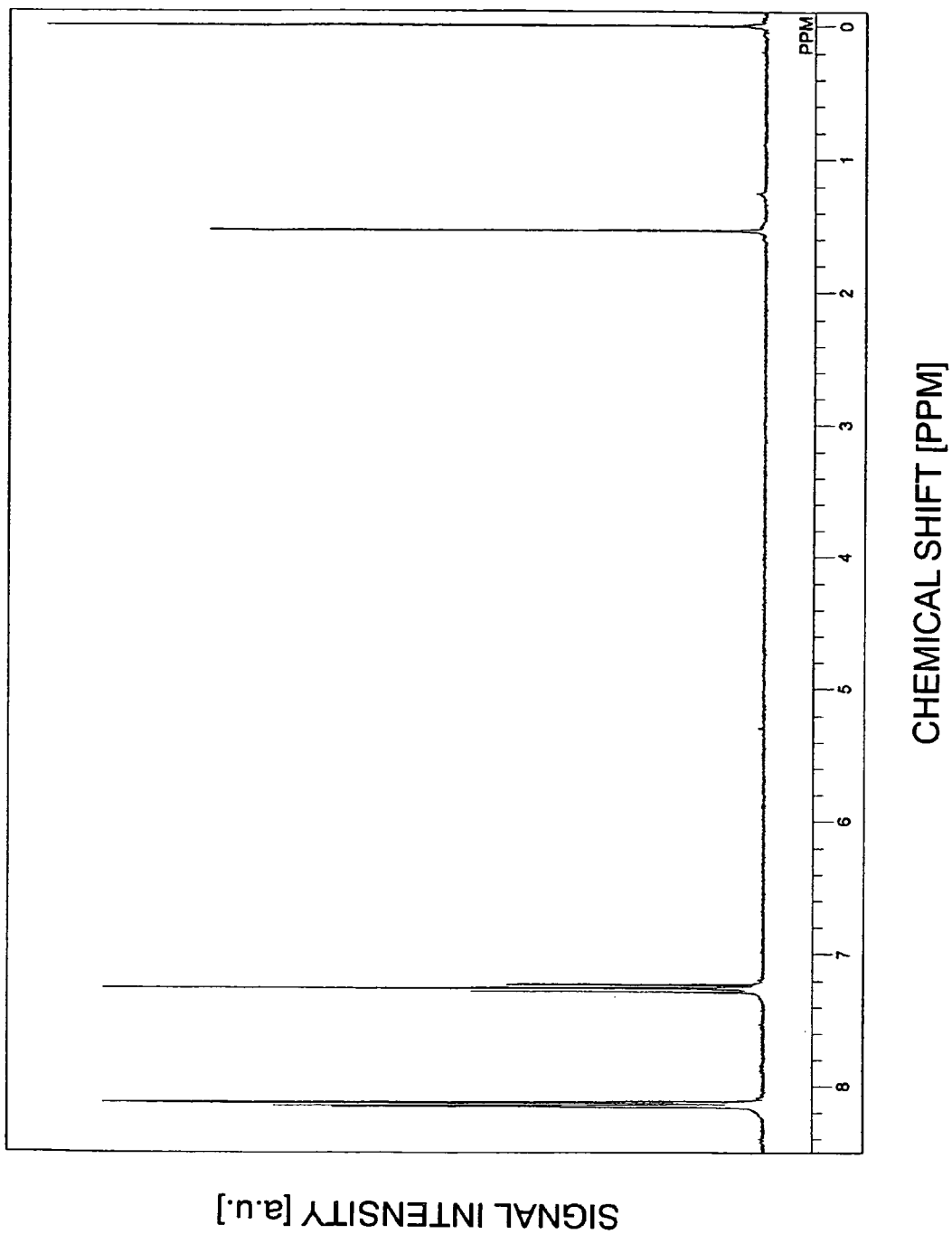
FIG. 7 shows ¹H NMR chart of 1,5-diiodo naphthalene that is an intermediate.

Concentrated sulfuric acid (25 mL) solution of NaNO₂ (3 g) was slowly dropped into a glacial acetic acid (25 mL) solution of 1,5-diamino naphthalene (3 g) at 0° C. After dropping, a reaction mixture was stirred at 0° C. for fifteen minutes. The reaction mixture was slowly added into ice of 50 g which included urea of 250 mg. Then a water solution (100 mL) of KI (potassium iodide) (100 g) was slowly dropped. After dropping, the reacted solution was agitated at a room temperature for overnight. The precipitated solid matter was collected by suction filtration and dried in a vacuum. Then, the solid matter was extracted using dichloromethane and a portion that had been dissolved in dichloromethane was concentrated. The thus obtained solid matter was purified with silica gel chromatography (hexane: dichloromethane=3:1) and recrystallized with dichloromethane/hexane to obtain 1,5-diiodo naphthalene as a light-yellow powered solid matter (2.3 g) with a yield of 32%. NMR data is shown below. $^1$H NMR (300 MHz, CDCl₃) d ppm: 8.16-8.12 (m, 4H), 7.25 (d, 2H, J=7.8 Hz). FIG. 7 shows a chart of $^1$H NMR of obtained 1,5-diiodo naphthalene.

Figure 8:
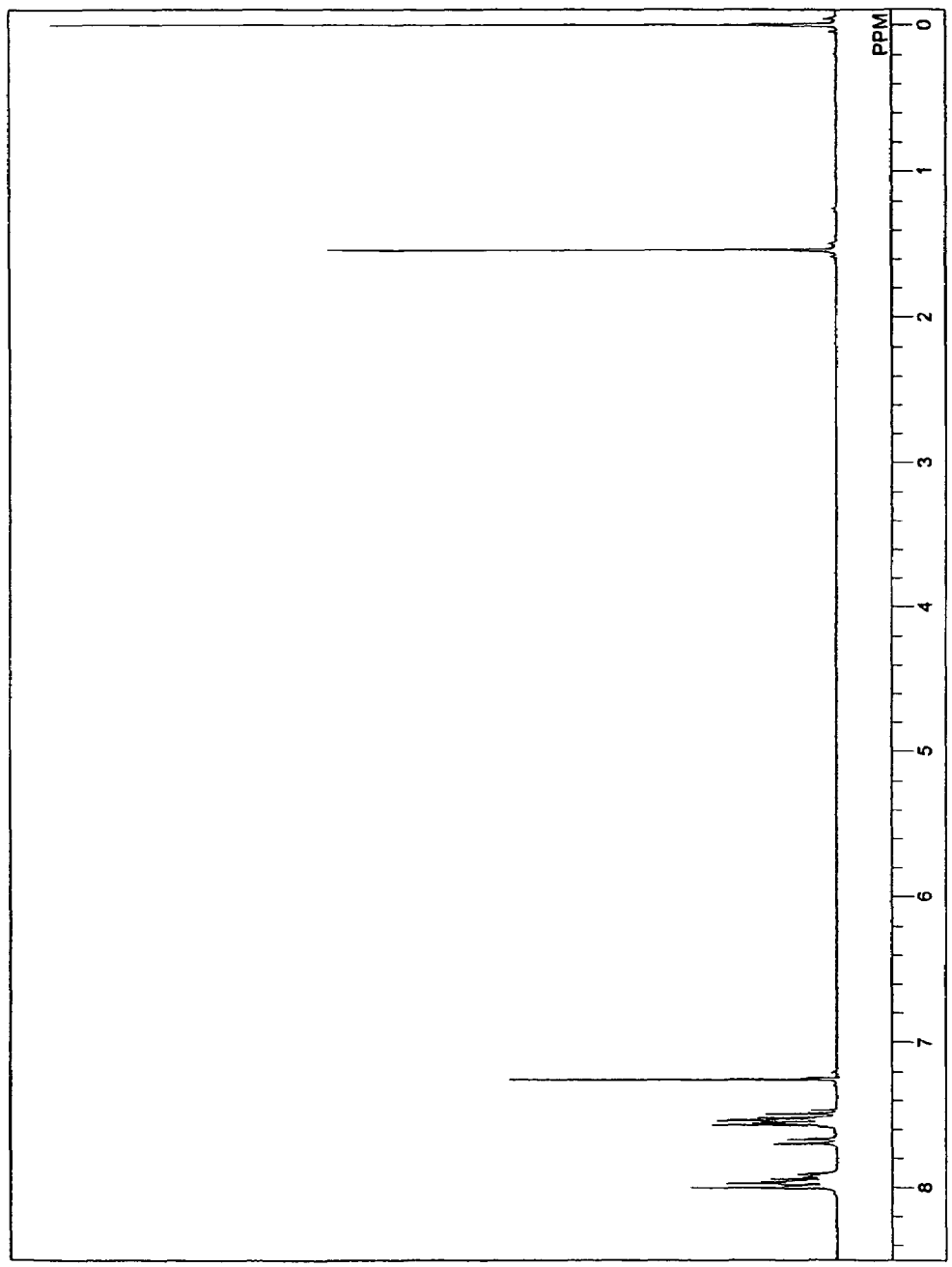
FIG. 8 shows ¹H NMR chart of 1,5-di(2-naphthyl)naphthalene that is an oligonaphthalene derivative according to one aspect of the present invention.

The obtained 1,5-diiodo naphthalene of 2.0 g (5.3 mmol), naphthyl-2-boronic acid of 2.0 g (11.6 mmol), palladium acetate of 27 mg (0.053 mmol), and tri(2-tolyl)phosphine of 67 mg (0.21 mmol) were added into a 100 ml three-neck flask and was exposed to a nitrogen gas stream. Then, 20 ml of ethylene glycol dimethyl ether was added. 10 ml of 2.0M potassium carbonate solution was added thereto and it was stirred at 80° C. for four hours. After reaction, a reaction solution was washed with water three times and a water layer was extracted with toluene three times. It was washed together with an organic layer by saturated saline and then, dried by magnesium sulfate, filtered naturally and the filtrate was concentrated. When the thus solid matter was purified by alumina column chromatography (toluene) and recrystallized by toluene, an object, i.e., DNN1 of 1.8 g was obtained with the yield of 90% as an achromatic plate-like crystal. NMR data is shown below. $^1$H NMR (300 MHz, CDCl₃) d ppm: 8.00-7.91 (m, 10H), 7.70-7.67 (m, 2H), 7.59-7.47 (m, 8H). FIG. 8 shows a chart of $^1$H NMR of the obtained DNN1.

Figure 3:
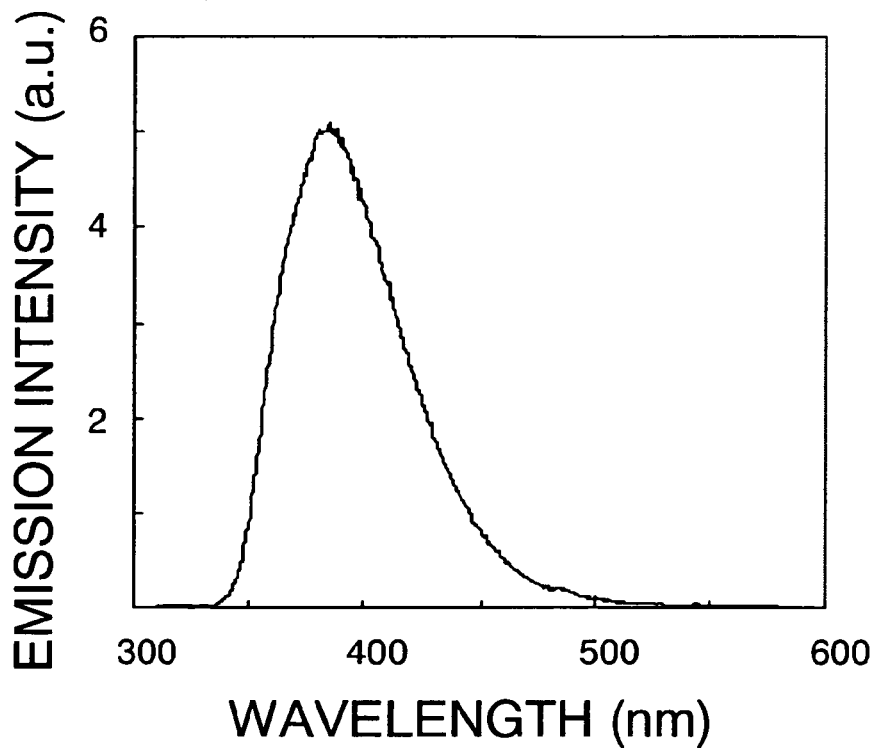
FIG. 3 shows an emission spectrum of 1,5-di(2-naphthyl)naphthalene that is an oligonaphthalene derivative according to one aspect of the present invention.

The obtained DNN1 was measured in the same way as in Example 1. The maximum absorption wavelength of thin film DNN1 was 255 nm. In addition, as shown in FIG. 3, it could be known that the maximum emission wavelength of thin film DNN1 was 384 nm and thus, light in a short wavelength was obtained. The melting point of the DNN1 is 237° C. HOMO level and LUMO level were −5.74 eV and −2.62 eV, respectively, and thus the extremely large band gap of 3.1 eV was obtained.

EXAMPLE 3

Example 3 describes a synthesizing method of a compound shown by structural formula (64) i.e., 1,4-di(2-naphthyl) naphthalene (DNN2) as one example of a material according to the present invention.

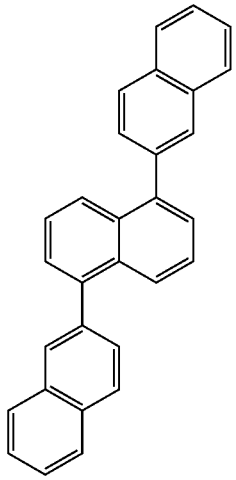

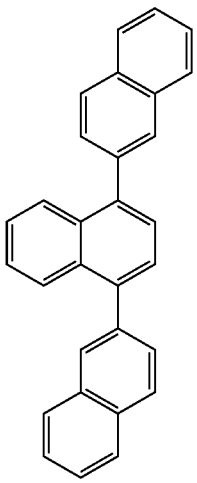
(64)

Synthesis scheme of 1,4-di(2-naphthyl)naphthalene (DNN2) is shown by (A-3).

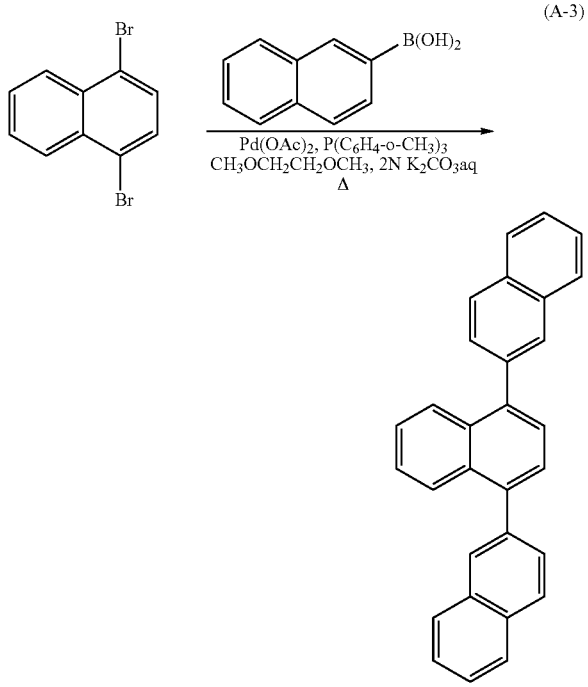

Figure 9:
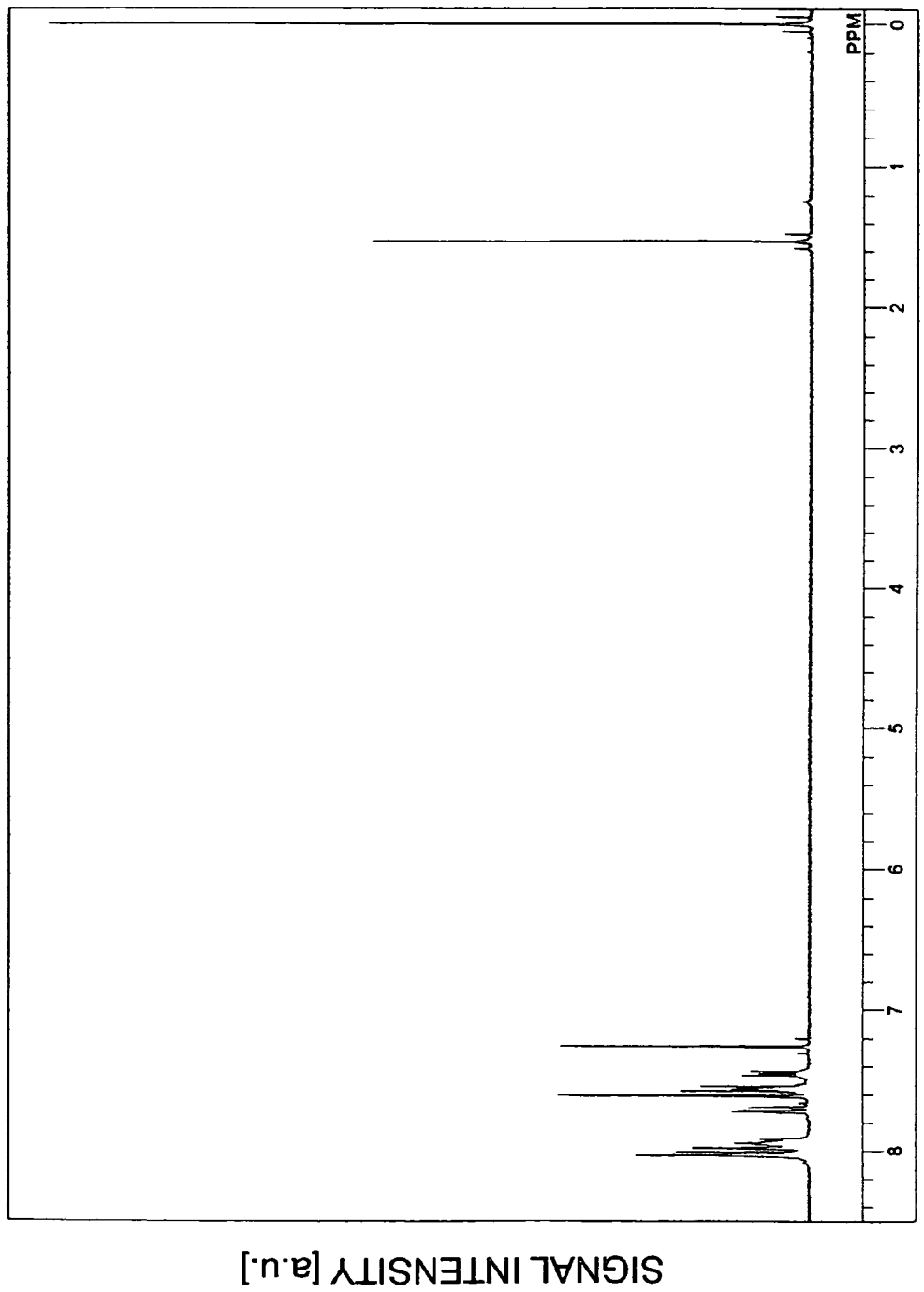
FIG. 9 shows ¹H NMR chart of 1,4-di(2-naphthyl)naphthalene that is an oligonaphthalene derivative according to one aspect of the present invention.

The 1,4-diiodo naphthalene of 5.0 g (17.5 mmol), 2-naphthalene boronic acid of 6.6 g (38.5 mmol), palladium acetate of 42 mg (0.175 mmol), and tri(2-tolyl) phosphine of 213 mg (0.70 mmol) were added to a 300 ml three-neck flask and was exposed to a nitrogen gas stream, then, 80 ml of ethylene glycol dimethyl ether was added. 20 ml of 2.0M potassium carbonate solution was added thereto and it was stirred at 80° C. for four hours. After reaction, a reaction solution was washed with water three times and a water layer was extracted with toluene three times. It was washed together with an organic layer by saturated saline and then, dried by magnesium sulfate, filtered naturally and concentrated. The thus obtained solid matter was purified by alumina column chromatography (toluene), the obtained solution was concentrated and then the obtained solid matter was recrystallized with toluene. Thus, an object, i.e., DNN2 of 5.3 g was obtained with the yield of 80% as an achromatic plate-like crystal. NMR data is shown below. $^1$H NMR (300 MHz, CDCl$_3$) d ppm: 8.05-7.92 (m, 10H); 7.23-7.69 (m, 2H), 7.61 (s, 2H), 7.58-7.55 (m, 4H) and 7.47-7.43 (m, 2H). FIG. 9 shows a chart of $^1$H NMR of the obtained DNN2.

Figure 4:
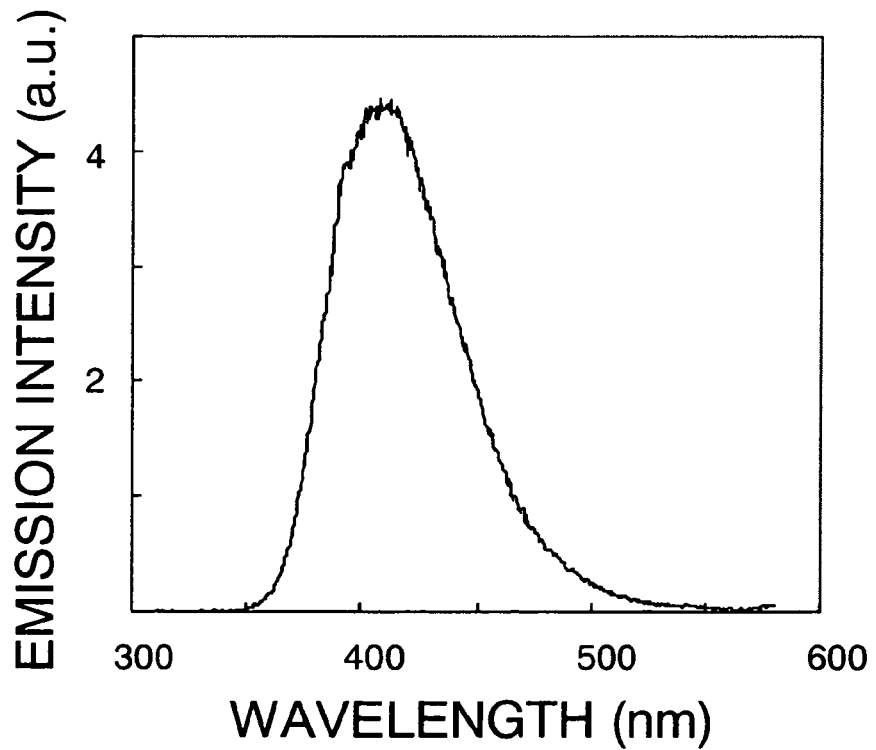
FIG. 4 shows an emission spectrum of 1,4-di(2-naphthyl)naphthalene that is an oligonaphthalene derivative according to one aspect of the present invention.

The obtained DNN2 was measured in the same way as in Example 1. The maximum absorption wavelength of thin film state was 296 nm. In addition, as shown in FIG. 4, it could be known that the maximum emission wavelength of thin film state was 408 nm and thus, light in a short wavelength was obtained. The melting point of the DNN1 is 237° C. HOMO level and LUMO level were −5.85 eV and −2.63 eV, respectively, and thus the extremely large band gap of 3.2 eV was obtained.

EXAMPLE 4

Figure 10:
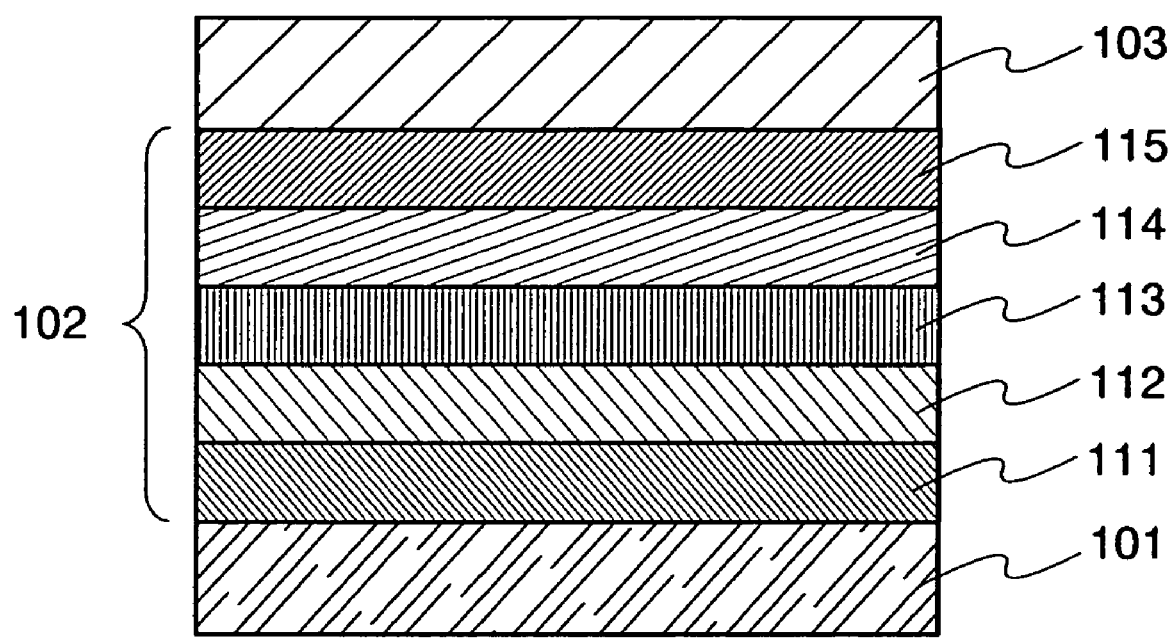
FIG. 10 shows an example of a light-emitting element according to one aspect of the present invention.

In Example 4, a light-emitting element using DNBN2 shown by structural formula (94) with reference to FIG. 10 is described.

Indium tin oxide including silicon was formed as the first electrode 101. Thereover, 4,4'-bis[N-{4-(N,N-bis(3-methylphenyl)amino)phenyl}N-phenylamino]biphenyl (DNTPD) having a thickness of 50 nm was formed to function as the hole injecting layer 111.

On the DNTPD film, 4,4'-bis[N-(1-naphthyl)-N-phenylamino]biphenyl (NPB) having a thickness of 30 nm was formed to be function as the hole transporting layer 112. These films were both formed by a vacuum evaporation method.

On this NPB film, DNBN2 and 2,5,8,11-tetra-t-butyl perylene (TBP) were formed by a co-evaporation method. This film served as the light-emitting layer 113 and was 40 nm thick. Further, the concentration of TBP with respect to DNBN2 was 1 wt %.

A light-emitting element was formed by depositing Alq with a thickness of 20 nm serving as the electron transporting layer 114, calcium fluoride with a thickness of 1 nm serving as the electron injecting layer 115, and last, Al with a thickness of 100 nm serving as the second electrode 103 over the light-emitting layer 113.

When a current was applied to the manufactured light-emitting element, luminescence with excellent color purity of blue with CIE chromaticity coordinate (x=0.15, y=0.12) could be obtained.

EXAMPLE 5

Example 5 describes a light-emitting element using DNN1 shown by structural formula (34) with reference to FIG. 10.

Indium tin oxide including silicon was formed as the first electrode 101. Thereon, copper phthalocyanine (CuPc) having a thickness of 20 nm was formed to function as the hole injecting layer 111.

On this CuPc film, 4,4'-bis[N-(1-naphthyl)-N-phenylamino]biphenyl (NPB) having a thickness of 40 nm was formed to function as the hole transporting layer 112. These films were each formed by a vacuum evaporation method.

On this NPB film, DNN1 and 2,-t-butyl-9,10-di(2-naphthyl)anthracene (t-BuDNA) were formed by a co-evaporation method. This film served as the light-emitting layer 113 and was 40 nm thick. Further, the weight ratio of t-BuDNA and DNN1 was 1:1.

A light-emitting element was formed by depositing Alq with a thickness of 20 nm serving as the electron transporting layer 114, calcium fluoride with a thickness of 1 nm serving as the electron injecting layer 115, and last, Al with a thickness of 100 nm serving the second electrode 103 over the light-emitting layer 113.

When a current was applied to the manufactured light-emitting element, luminescence with excellent color purity of blue with CIE chromaticity coordinate (x=0.16, y=0.16) was obtained.

EXAMPLE 6

Example 6 describes a light-emitting element using DNN2 shown by structural formula (64) with reference to FIG. 10.

Indium tin oxide including silicon was formed as the first electrode 101. Thereon, copper phthalocyanine (CuPc) having a thickness of 20 nm was formed to function as the hole injecting layer 111.

On this CuPc film, 4,4'-bis[N-(1-naphthyl)-N-phenylamino]biphenyl (NPB) having a thickness of 40 nm was formed to function as the hole transporting layer 112. These films were each formed by a vacuum evaporation method.

Over this NPB film, DNN2 and 2,-t-butyl-9,10-di(2-naphthyl)anthracene (t-BuDNA) were formed by a co-evaporation method. This film served as the light-emitting layer 113 and was 40 nm thick. Further, the weight ratio of t-BuDNA and DNN2 was 1:1.

A light-emitting element was formed by depositing Alq with a thickness of 20 nm serving as the electron transporting layer 114, calcium fluoride with a thickness of 1 nm serving as the electron injecting layer 115, and last, Al with a thickness of 100 nm serving the second electrode 103 over the light-emitting layer 113.

When a current was applied to the manufactured light-emitting element, luminescence with excellent color purity of blue with CIE chromaticity coordinate (x=0.15, y=0.12) was obtained.

EXAMPLE 7

Example 7 describes a light-emitting element using DNBN2 shown by structural formula (94) as a dopant with reference to FIG. 10.

Indium tin oxide including silicon was formed as the first electrode 101. Thereon, copper phthalocyanine (CuPc) having a thickness of 20 nm was formed to function as the hole injecting layer 111.

On this CuPc film, 4,4'-bis[N-(1-naphthyl)-N-phenylamino]biphenyl (NPB) having a thickness of 40 nm was formed to function as the hole transporting layer 112. These films were both formed by a vacuum evaporation method.

On this NPB film, DNBN2 and tetraphenyl silane (TPS) were formed by a co-evaporation method. This film served as the light-emitting layer 113 and was 40 nm thick. Further, the weight ratio of DNBN2 and TPS was 1:100.

A light-emitting element was formed by depositing Alq with a thickness of 20 nm serving as the electron transporting layer 114, calcium fluoride with a thickness of 1 nm serving as the electron injecting layer 115, and last, Al with a thickness of 100 nm serving the second electrode 103 over the light-emitting layer 113.

When a current was applied to the manufactured light-emitting element, luminescence from DNBN2 was obtained.

EXAMPLE 8

Example 8 describes various electronic devices each including a light-emitting device formed using a light-emitting element of the present invention as a part thereof.

Electronic devices manufactured using a light-emitting device having a light-emitting element of the present invention are, for example, a camera such as a video camera or a digital camera, a goggle type display, a navigation system, a sound reproduction device (such as a car audio or an audio component), a computer, a game machine, a mobile information terminal (such as a mobile computer, a cell phone, a portable game machine, or an electronic book), an image reproduction device (such as a device which can reproduce a recording medium such as a digital versatile disk (DVD) and is equipped with a display device capable of displaying the image) and the like. These electronic devices are specifically shown in FIGS. 12A to 12E.

Figure 12A:
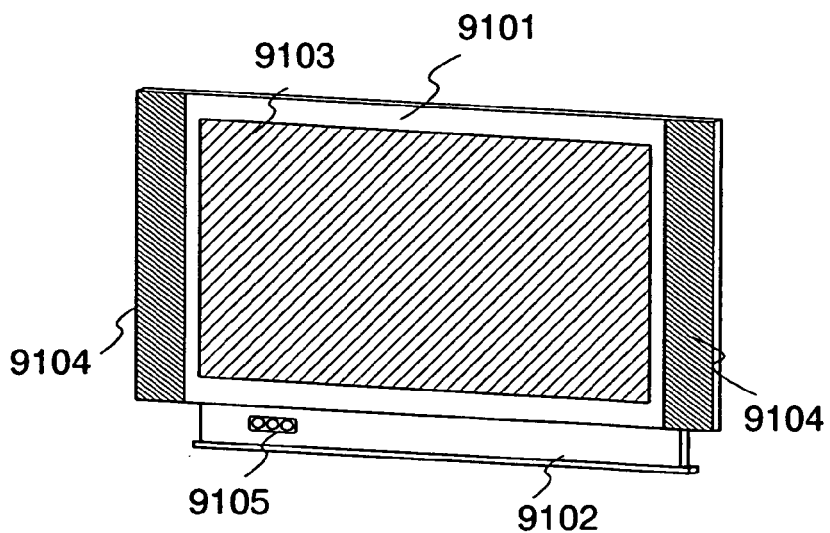
FIGS. 12A to 12E each show an electronic device according to one aspect of the present invention.

FIG. 12A shows a television receiving machine including a casing 9101, a supporting stand 9102, a display portion 9103, speaker portions 9104, a video input terminal 9105, and the like. The television receiving machine of the present invention is manufactured by using a light-emitting device having a light-emitting element of the present invention for the display portion 9103. Since the light-emitting device of the present invention employs an oligonaphthalene derivative of the present invention, luminescence of blue with excellent color purity can be obtained. It is to be noted that the television receiving machine includes all types of information display devices, e.g., a display device for a computer, one for TV broadcast reception, one for advertisement display, and so on.

Figure 12B:
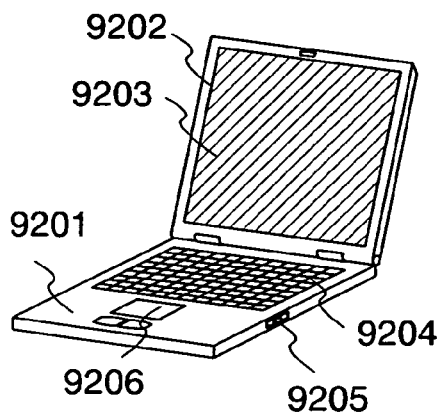

FIG. 12B shows a computer including a main body 9201, a casing 9202, a display portion 9203, a keyboard 9204, an external connection port 9205, a pointing mouse 9206, and the like. The computer of the present invention is manufactured by using a light-emitting device having a light-emitting element of the present invention for the display portion 9203. Since the light-emitting device of the present invention employs an oligonaphthalene derivative of the present invention, luminescence of blue with excellent color purity can be obtained. Therefore, color reproducibility is enhanced and a crisp and clean image can be displayed.

Figure 12C:
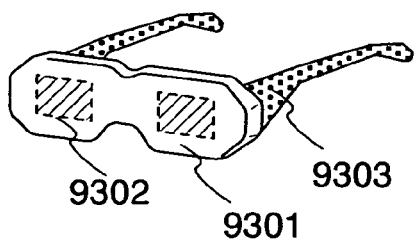

FIG. 12C shows a goggle-type display including a main body 9301, display portions 9302, arm portions 9303, and the like. The goggle-type display of the present invention is manufactured by using a light-emitting device having a light-emitting element of the present invention for the display portion 9302. Since the light-emitting device of the present invention employs an oligonaphthalene derivative of the present invention, luminescence of blue with excellent color purity can be obtained. Therefore, color reproducibility is enhanced and a crisp and clean image can be displayed.

Figure 12D:
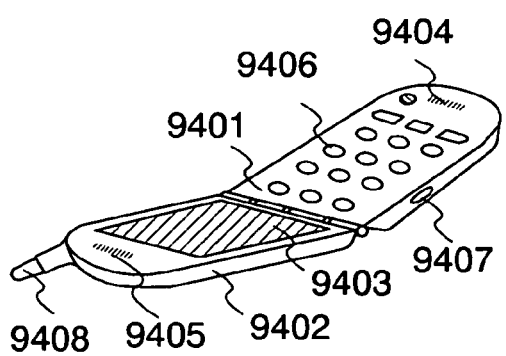

FIG. 12D shows a cell phone including a main body 9401, a casing 9402, a display portion 9403, an audio input portion 9404, an audio output portion 9405, operation keys 9406, an external connection port 9407, an antenna 9408, and the like. The cell mobile phone of the present invention is manufactured by using a light-emitting device having a light-emitting element of the present invention for the display portion 9403. Since the light-emitting device of the present invention employs an oligonaphthalene derivative of the present invention, luminescence of blue with excellent color purity can be obtained. Therefore, color reproducibility is enhanced and a crisp and clean image can be displayed.

Figure 12E:
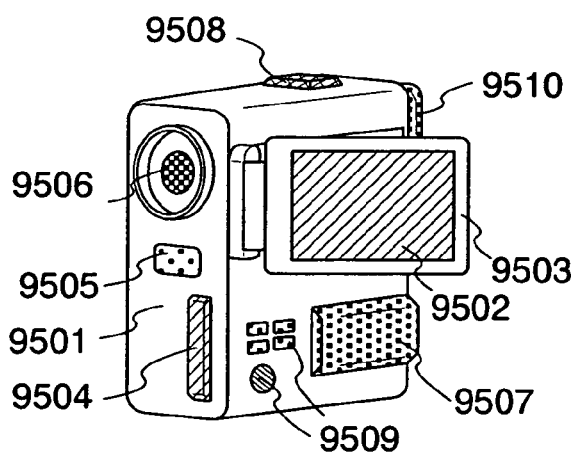

FIG. 12E shows a camera including a main body 9501, a display portion 9502, a casing 9503, an external connection port 9504, a remote control receiving portion 9505, an image receiving portion 9506, a battery 9507, an audio input portion 9508, operation keys 9509, an eyepiece portion 9510, and the like. The camera of the present invention is manufactured by using a light-emitting device having a light-emitting element of the present invention for the display portion 9502. Since the light-emitting device of the present invention employs an oligonaphthalene derivative of the present invention, luminescence of blue with excellent color purity can be obtained. Therefore, color reproducibility is enhanced and a crisp and clean image can be displayed.

As thus described, a light-emitting device having a light-emitting element according to the present invention can be applied in an extremely wide range, and the light-emitting device can be applied to electronic devices of every field. By using a light-emitting device having a light-emitting element of the present invention, electronic devices having superior color reproductively can be provided.

What is claimed is:

1. An oligonaphthalene derivative represented by a formula (29):

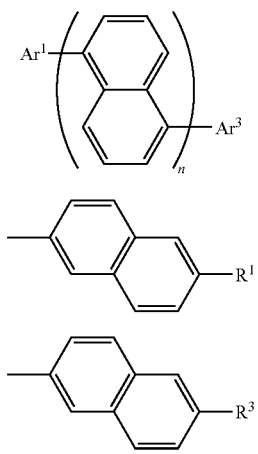

n is 2,
Ar$^1$ is a substituent represented by a formula (31), and Ar$^3$ is a substituent represented by a formula (33); and
each of R$^1$ and R$^3$ is an ester group or a carbonyl group.

2. A light-emitting element comprising:
a layer including a luminescent material between a pair of electrodes,
wherein the layer including the luminescent material comprises an oligonaphthalene derivative represented by a formula (29):

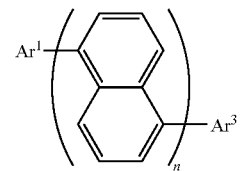

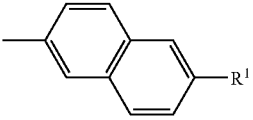

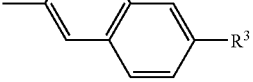

n is 2,
Ar$^1$ is a substituent represented by a formula (31), and Ar$^3$ is a substituent represented by a formula (33); and
each of R$^1$ and R$^3$ is an ester group or a carbonyl group.

3. An electronic device comprising the light-emitting element according to claim 2,
wherein the electronic device is one of a camera, a goggle type display, a navigation system, a sound reproduction device, a computer, a game machine, a mobile information terminal, and an image reproduction device.

* * * * *